US012788957B2

United States Patent

(12) United States Patent
Azeloglu et al.

(10) Patent No.: US 12,788,957 B2
(45) Date of Patent: Nov. 10, 2026

(54) VASCULAR ACCESS DEVICES WITH SELF-SEALING VALVES

(71) Applicant: ICAHN SCHOOL OF MEDICINE AT MOUNT SINAI, New York, NY (US)

(72) Inventors: Evren Azeloglu, New York, NY (US); Eric Lima, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 447 days.

(21) Appl. No.: 18/563,618

(22) PCT Filed: May 27, 2022

(86) PCT No.: PCT/US2022/031321
§ 371 (c)(1),
(2) Date: Nov. 22, 2023

(87) PCT Pub. No.: WO2022/251616
PCT Pub. Date: Dec. 1, 2022

(65) Prior Publication Data

US 2024/0238575 A1 Jul. 18, 2024

Related U.S. Application Data

(60) Provisional application No. 63/194,428, filed on May 28, 2021.

(51) Int. Cl.
*A61M 39/02* (2006.01)
*A61M 39/06* (2006.01)

(52) U.S. Cl.
CPC ........ *A61M 39/0247* (2013.01); *A61M 39/06* (2013.01); *A61M 39/0606* (2013.01);
(Continued)

(58) Field of Classification Search
CPC .............. A61M 39/0247; A61M 39/06; A61M 39/0606; A61M 39/0208;
(Continued)

(56) References Cited

U.S. PATENT DOCUMENTS 4,886,501 A 12/1989 Johston et al.
6,319,226 B1 11/2001 Sherry
(Continued)

OTHER PUBLICATIONS

International Search Report and Written Opinion in PCT Application No. PCT/US2022/031321, mailed Oct. 5, 2022 (12 pages).
(Continued)

*Primary Examiner* — Tasnim Mehjabin Ahmed
(74) *Attorney, Agent, or Firm* — Leason Ellis LLP

(57) ABSTRACT

A vascular access device is implanted under the skin directly over a vascular structure, such as a blood vessel that makes up the arteriovenous (AV) fistula. The vascular access device is designed such that insertion of and the travel of a needle, such as a standard dialysis needle, within a needle access channel urges a displaceable valve to an open position and removal of the dialysis needle from the channel results in the valve automatically closing and sealing the wound, thereby preventing back-bleeding.

42 Claims, 36 Drawing Sheets

(52) U.S. Cl.
CPC ............... *A61M 2039/0258* (2013.01); *A61M 2039/0261* (2013.01); *A61M 2039/027* (2013.01); *A61M 2039/0273* (2013.01); *A61M 2039/0276* (2013.01); *A61M 2039/0294* (2013.01); *A61M 2039/062* (2013.01)

(58) Field of Classification Search
CPC .. A61M 2039/0258; A61M 2039/0261; A61M 2039/027; A61M 2039/0273; A61M 2039/0276; A61M 2039/0294; A61M 2039/062
See application file for complete search history.

(56) References Cited

U.S. PATENT DOCUMENTS

| | | | | |
|---|---|---|---|---|
| 7,223,257 | B2 | 5/2007 | Shubayev et al. | |
| 2002/0013557 | A1* | 1/2002 | Sherry .............. | A61M 39/0208 604/288.03 |
| 2005/0209573 | A1 | 9/2005 | Brugger et al. | |
| 2007/0016162 | A1* | 1/2007 | Burbank ........... | A61M 39/0208 604/288.03 |
| 2018/0280676 | A1* | 10/2018 | Achard de la Vente ..................... | A61M 39/0208 |
| 2019/0046233 | A1 | 2/2019 | Feng et al. | |

OTHER PUBLICATIONS

Extended European Search Report in EP Application No. 22812247.9-1122/4346984, mailed Mar. 7, 2025 (7 pages).

* cited by examiner

VASCULAR ACCESS DEVICES WITH SELF-SEALING VALVES

CROSS REFERENCE TO RELATED APPLICATION

The present application is a U.S. National Phase Application under 35 U.S.C. § 371 of International Patent Application No. PCT/US2022/031321, filed on May 27, 2022, which claims the benefit of and priority to U.S. patent application Ser. No. 63/194,428, filed May 28, 2021, all of which are incorporated by reference as if expressly set forth in their respective entireties herein.

TECHNICAL FIELD

The present disclosure is directed to vascular access devices and more particularly, to self-sealing vascular access devices that can, in one embodiment, be in the form of a self-sealing dialysis access device that is implanted under the skin directly over the blood vessel that makes up the arteriovenous (AV) fistula. The vascular access device is designed such that insertion of and the travel of a needle, such as a standard dialysis needle, within a needle access channel urges a valve to an open position and removal of the dialysis needle from the channel results in the valve automatically closing and sealing the wound, thereby preventing back-bleeding.

BACKGROUND

Vascular access devices are very commonly used and are inserted into veins via peripheral or central vessels for diagnostic or therapeutic reasons, such as blood sampling, central venous pressure readings, administration of medication, fluids, total parenteral nutrition (TPN) and blood transfusions.

One field in which vascular access is required is the treatment of dialysis patients. A dialysis treatment is a procedure to remove waste products and excess fluid from the blood when the kidneys stop working properly. It often involves diverting blood to a machine (dialyzer) to be cleaned. To get the patient's blood into the dialyzer, the doctor needs to make an access, or entrance, into the patient's blood vessels. For example, a vascular access is a surgically created vein used to remove and return blood during hemodialysis. An arteriovenous (AV) fistula is a connection, made by a vascular surgeon, of an artery to a vein.

Currently, cannulation of dialysis patients with AV fistulae needs to be performed by highly trained specialists in order to preserve the integrity of the vessels that are accessed three times a week. Despite the expertise, access-related adverse events remain a major obstacle in expanding dialytic care. Even though frequent (e.g., daily) dialysis is known to have more favorable outcomes, it has been shown that increased hemodialysis frequency also leads to more access failure/repairs or hospitalizations. Accordingly, the current limiting factor to positive medical outcomes in hemodialysis is reliable vascular access device. In sum, prior vascular access devices have not been able to address the increased risk for bleeding or infection.

SUMMARY

A self-sealing vascular access device according to one embodiment includes an implantable base having a top surface and an opposite bottom surface. The implantable base has a valve compartment defined therein and also has a needle access channel formed therein. The needle access channel is open along both the top surface and the bottom surface of the implantable base and the valve compartment is open to the needle access channel. The self-sealing vascular access device also includes a displaceable valve that is disposed within the valve compartment and is movable between a lowered (closed) position in which the displaceable valve blocks and seals the needle access channel and a raised (open) position in which the displaceable valve is spaced from the needle access channel resulting in opening of the needle access channel to allow travel of the needle to the target vascular site.

As described herein, the present vascular access devices are intended for implantation under the skin (subcutaneous tissue) of the patient above a target vascular structure (e.g., blood vessel) that is to be pierced by a cannula (e.g., a needle). The implantable vascular access devices not only are configured for controlled delivery of the cannula (needle) to the target vascular structure and thus act as a guide but also have a self-sealing valve that moves between open and closed positions without user involvement or user intervention. The self-sealing valve is configured to automatically open upon insertion and travel of the cannula within the vascular access device and subsequently, upon removal of the cannula from the vascular access device, the valve automatically closes to seal the wound and prevent back-bleeding. As described herein and according to certain embodiments, the valve returns to its closed position by: 1) the pressure exerted on the top surface of the valve by the subcutaneous tissue; 2) through the force of a biasing element (e.g., spring); or 3) by both the pressure differential on the top and bottom surfaces of the valve and the force of the biasing element.

In one exemplary application, the vascular access device comprises a self-sealing dialysis access device that is used to deliver a standard dialysis needle to the blood vessel that makes up the AV fistula. This application is intended, in at least one application, for at home dialysis patients.

BRIEF DESCRIPTION OF THE DRAWING FIGURES

DETAILED DESCRIPTION OF CERTAIN EMBODIMENTS

Figure 1:
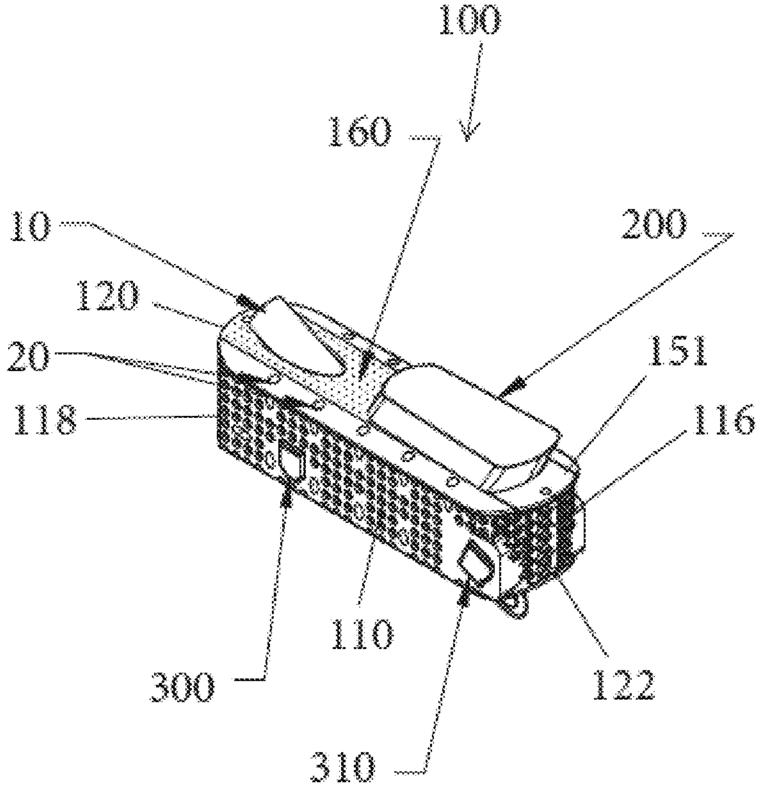
FIG. 1 is a top and side perspective view of a vascular access device (e.g., a self-sealing dialysis access device) in accordance with a first embodiment.
Figure 2:
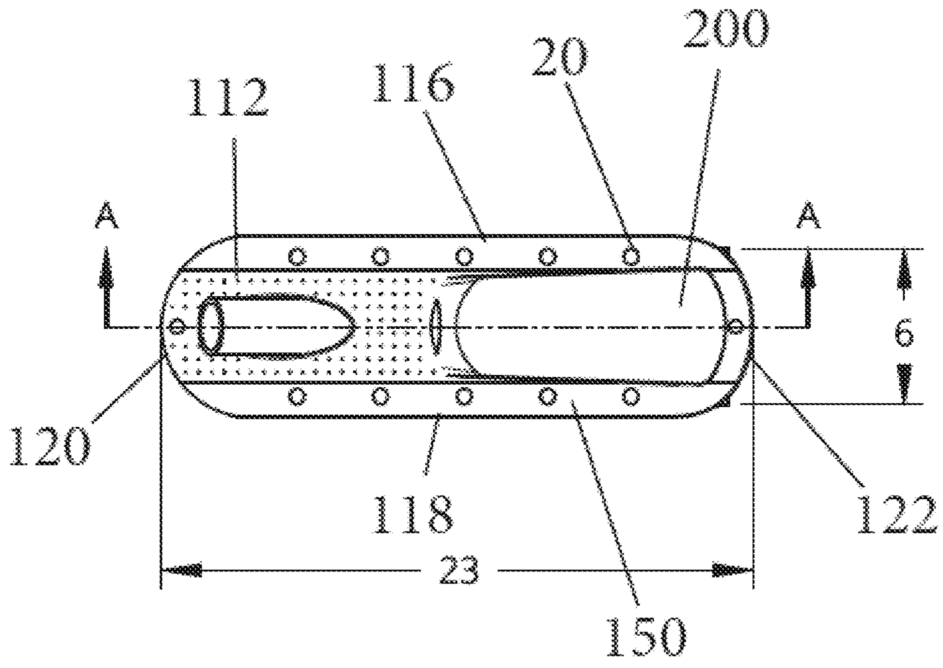
FIG. 2 is a top plan view thereof.
Figure 3:
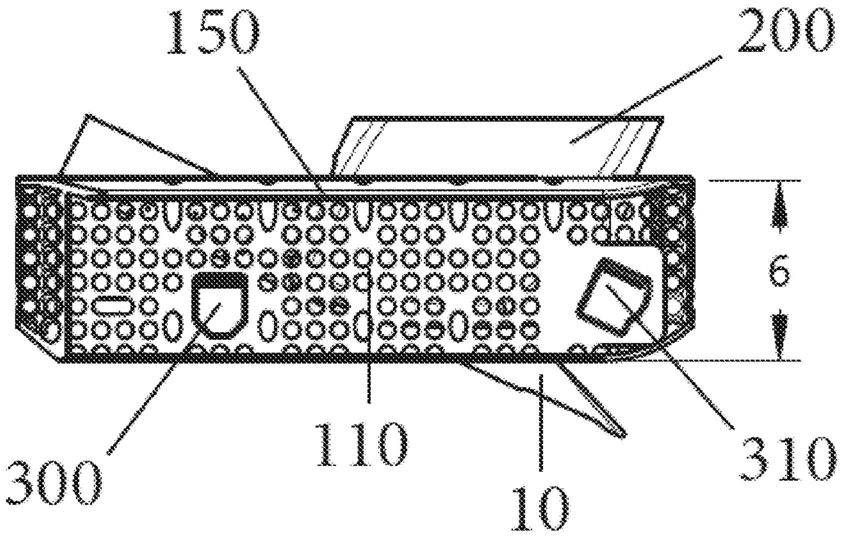
FIG. 3 is a side elevation view thereof.
Figure 4:
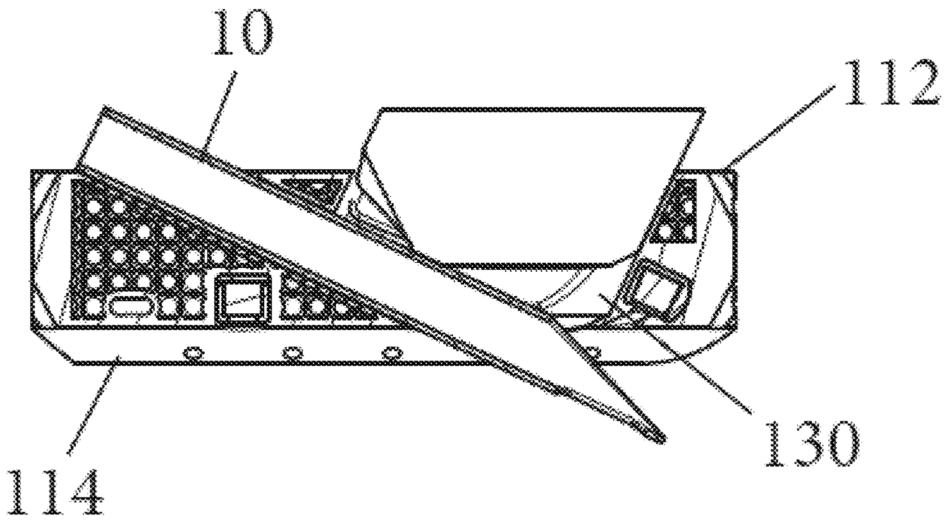
FIG. 4 is a cross-sectional view taken along the line A-A of FIG. 2.

As mentioned, the present disclosure sets forth various vascular access devices that are intended for implantation under the skin of the patient above a target vascular structure (e.g., blood vessel) that is to be pierced by a cannula (e.g., a needle). The implantable vascular access devices not only are configured for controlled delivery of the cannula (needle) to the target vascular structure but also have a self-sealing valve that moves between an open and closed position without user involvement or user intervention. The self-sealing valve is configured to automatically open upon insertion and travel of the cannula within the vascular access device and subsequently, upon removal of the cannula from the vascular access device, the valve automatically closes to seal the wound and prevent back-bleeding. As described herein and according to certain embodiments, the valve returns to its closed position by: 1) the pressure exerted on the top surface of the valve by the subcutaneous tissue; 2) through the force of a biasing element (e.g., spring); or 3) by both the pressure differential on the top and bottom surfaces of the valve and the force of the biasing element.

In one embodiment, the vascular access device comprises a self-sealing dialysis access device that is designed to help guide cannulation during dialysis. The device is intended to be implanted under the skin directly over the blood vessel that makes up an arteriovenous (AV) fistula. The device is configured to accept a standard dialysis needle through an opening on the top of the device and guides the needle at a fixed angles toward the blood vessel that lies below the device. The device enables repeated entry into the fistula through the same location with minimal risk of damage and hemorrhages. Upon withdrawal of the needle, a collinear valve that is mechanically displaced during needle entry seals the wound and prevents back-bleeding. The collinear valve mechanism relies on the needle guide geometry and no motorized components are necessary for its operation. Immediate closure of the fistula access will likely reduce bleeding risk (which is a major adverse event associated with hemodialysis); enable faster healing; and lower the risk of infection.

The disclosed vascular access devices contain a number of advantageous features, including but not limited to: 1) a self-sealing collinear valve; 2) an optional internal 3D printed one piece spring mechanism; 3) metallic foam for tissue integration; 4) optional functional sensor arrangement that detects needle entry; 5) ergonomic shape for easy implantation and minimal erosion/tissue damage; and 6) safety features to prevent dislodgement.

It will be appreciated that while the vascular access devices are described herein as being self-sealing dialysis access devices, the disclosed vascular access devices are not limited to dialysis applications but can be used in other suitable applications as well. Thus, dialysis applications are only exemplary in nature and not limiting of the scope of the present devices and the present disclosure.

Vascular Access Device 100

Now referring to FIGS. 1-10, a vascular access device 100 according to one exemplary embodiment is shown and comprises an implantable base 110 that has a top surface 112, an opposite bottom surface 114, a first side 116, an opposite second side 118, a first end 120 and an opposite second end 122. When implanted, the top surface 112 faces the skin (subcutaneous tissue) of the patient and the bottom surface 114 faces the target vascular structure (e.g., blood vessel that makes up the AV fistula). The vascular access device 100 is configured to controllably deliver a cannula or needle 10 to a target site. In dialysis applications, the needle 10 comprises a standard dialysis needle, which can also be referred to as being a fistula cannula needle or fistula catheter needle.

In one example, the width of the implantable base 110 is about 6 mm and its length is about 23 mm. Since its implanted location is between the subcutaneous tissue and the blood vessel, the height of the implantable base 110 is sized accordingly. In one embodiment, the height is between about 5 mm and 9 mm. It will be understood that the aforementioned dimensions are only exemplary in nature and are not limiting of the scope of the present disclosure.

The implantable base 110 also includes several internal features such as a valve compartment 130 and a needle access channel 140. The needle access channel 140 is formed at a fixed angle within the implantable base 110 to allow the needle 10 to be inserted into the blood vessel at a desired angle. At a first end 142, the needle access channel 140 is open along the top surface 112 of the implantable base 110 and at an opposite second end 144, the needle access channel 140 is open along the bottom surface 114 of the implantable base 110. In one embodiment, as shown, the opening at the first end 142 can have an oblong shape and the opening at the second end 144 can have an oblong shape since the needle access channel intersects the top and bottom surfaces of the implantable base at an angle other than 90 degrees. The sizes and/or shapes of these openings can be the same, similar or different. In any event, as described below, these two openings at the opposite ends 142, 144 of the needle access channel 140 are configured to allow for insertion, travel and exiting of the needle 10.

The needle access channel 140 can thus be configured to receive the standard dialysis needle (or other type of needle) 10. The needle access channel 140 includes a curved bottom section 141 and a curved top section 143 which when combined define a circular or other shaped hole through which the standard dialysis needle 10 can pass. The curved top section 143 can have a shorter length compared to the curved bottom section 141 since the valve compartment 130 intersects the top section of the needle access channel 140 and thereby reduces the length of the top section 143. It will be appreciated that the top section 143 and bottom section 141 have a profile (e.g., curvature) in view of the shape of the needle that is for insertion into the needle access channel 140 and thus, the top section 143 and bottom section 141 can more generally be thought of as defining a bounded opening that comprises the needle access channel 140. The needle access channel 140 thus guides the needle 10 to the target vascular site at a fixed angle.

As shown in the figures, in at least one section of the needle access channel 140, the width (diameter) of the needle access channel 140 is equal to or only slightly greater than the width (diameter) of the standard dialysis needle 10 to provide an intimate relationship between these two parts (e.g., the two parts are at least substantially fluidly sealed relative to one another to prevent unintended fluid flow around the standard dialysis needle 10 within the needle access channel 140).

The standard dialysis needle 10, or other needle, is introduced into the open first end 142 of the needle access channel 140 and advances linearly within the needle access channel 140 before exiting the open second end 144 allowing insertion of the needle into the underlying blood vessel. The opening formed along the top surface 112 that permits access to the needle access channel 140 can be the same size or a different size compared to the opening formed along the bottom surface 114 to permit exiting of the needle 10. In addition, as shown, the open first end 142 can be formed so that it does not overlie the open second end 144 as a result of the angle at which the needle access channel 140 is formed in the implantable body 110.

The valve compartment 130 is formed in the implantable base 110 and is open along the top surface 112 as well as the bottom surface 114 to allow needle insertion and exit below the device. However, as shown, the opening along the top surface 112 can be significantly greater in area than the openings in the bottom surface 114. The valve compartment 130 can be defined by a first end wall 131 and an opposite second end wall 132. The first and second end walls 131, 132 can be angled (slanted) walls that are not formed perpendicular to the top and bottom surfaces 112, 114. The first end wall 131 can be a curved end wall and similarly, the second end wall 132 can be a curved end wall.

The walls of the valve compartment 130 are thus configured in view of the shape of the valve that is disposed therein. In addition, as described below, the walls of the valve compartment 130 are constructed to limit the movement of the valve within the valve compartment 130 and more particularly, prevent dislodgment of the valve from the valve compartment 130. Side walls of the valve compartment 130 can be planar walls that are formed at select angles. For example, the side walls can be non-parallel to one another.

The first end wall 131 intersects the top curved section 143. In the cross-sectional view of FIG. 10, the area between the top surface 112, the first end wall 131 and the curved top section 143 can have a generally triangular shape. The curved bottom section 141 lies at least partially below the valve compartment 130. This first end wall 131 is also designed to create an interference fit with the movable valve that is contained within the valve compartment as described herein for limiting and controlling movement of the valve. More specifically, as described below, the first end wall 131 prevents dislodgement of the valve from the valve compartment 130 when the valve moves from the closed position to the open position. The interference between the valve and the implantable base ensures that the valve only moves a prescribed distance to the fully raised (open) position and nothing more.

Moreover, a center longitudinal axis of the needle access channel 140 intersects the valve compartment 130 to allow for operation of the device 100 as described herein. More specifically, as described herein, the travel of the needle 10 within the needle access channel 140 serves as an actuating means for opening the valve and subsequent removal of the needle 10 from the need access channel 140 allows the valve to return to the closed position within the valve compartment 130.

The valve compartment 130 has a bottom section 139 that surrounds the open second end 144 of the needle access channel 140. The bottom section 139 can be thought of as at least partially defining a floor of the valve compartment 130. The bottom section 139 lies below the first and second end walls 131, 132. The bottom section 139 can at least in part have a beveled shape that is adjacent and surrounds the opening formed along the bottom of the implantable base 110 as shown.

As shown in the figures, in one embodiment, even when the side walls of the implantable base 110 have perforations, the side walls of the valve compartment 130 are preferably solid so as to prevent any ingress of foreign matter into the valve compartment 130 itself. Similarly, at least portions of the end walls 131, 132 can be solid.

As described herein and according to one embodiment, the implantable base 110 can be in the form of a block (a single integral body). The implantable base 110 can be formed using any number of conventional manufacturing techniques and in one embodiment, the implantable base 110 can be formed using 3D printer technology. 3D printer technology allows other features, such as the different compartments, channels, and spaces discussed herein, to easily be incorporated into the structure of the implantable base 110.

Suture Holes 20

In one embodiment, the implantable base 110 can be formed with suture holes 20 that receive suture material (not shown) for anchoring the device 100 at the target implant site. Sutures (not shown) can thus be used to anchor the device 100 to tissue along the top of the device and similarly anchor the device 100 to the underlying blood vessel along the bottom of the device. The suture holes 20 are formed along the periphery of the implantable base 110 and in the illustrated embodiment, the suture holes 20 are formed along at least two opposing edges of the implantable base 110 and preferably, are also formed along opposing sides and opposing ends of the implantable base 110.

The implantable base 110 can include a pair of side (peripheral) flanges 150 that define side edges of the top surface 112 and extend outwardly beyond the side walls of the implantable base 110. The top surface 112 can thus be thought of as having a center section 155 with the pair of side flanges 150 being formed on either side of the center section 155. The top openings into both the needle access channel 140 and the valve compartment 130 are formed within the center section 155. The side flanges 150 thus represent portions of the implantable base 110 that overhang the side walls thereof. The side flanges 150 extend linearly along the sides of the implantable base 110.

The side flanges 150 can include the suture holes 20 which are formed linearly along the length of the side flanges 150. The same number of suture holes 20 can be formed in each of the side flanges 150 and the suture holes 20 can be formed in pairs that are opposite one another. The suture holes 20 are therefore located beyond the sides of the implantable base 110 to permit passage of the suture material and allow the suture material to be anchored to surrounding tissue, etc. In the illustrated embodiment, there are five suture holes 20 on each side flange 150.

In addition, the implantable base 110 can optionally include at least one end flange 151 that is formed at one end of the implantable base 110. For example, the end flange 151 can be formed at the end of the implantable base 110 that is closest to the valve compartment 130. The end flange 151 overhangs the end of the implantable base 110 and can include one or more suture holes 20. In the illustrated embodiment, there are two end flanges 151 at the opposite ends of the implantable base 110 to allow ends of the implantable base 110 to be anchored to tissue using sutures.

The bottom of the implantable base 110 can include a similar peripheral flange structure that surrounds the sides and ends of the implantable body 110 and includes suture holes for suturing the device 100 to the blood vessel wall. As a result, the implantable body 110 can be sutured to both the blood vessel wall and the skin to anchor the implantable body 110 in place.

While the suture holes 20 are shown as circular shaped openings, it will be appreciated that the suture holes 20 can take any number of other shapes so long as suture material can pass through the openings.

Fenestrations 160

The device 100 can optionally include fenestrations 160 for promoting tissue ingrowth and additional anchoring of the device 100 at the target site. As is known, fenestrations 160 comprise an arrangement of openings formed in a substrate, such as one or more walls or surfaces of the device 100. In one exemplary embodiment, the fenestrations 160 can be formed in at least a portion of the top surface 112 and more particularly, the fenestrations 160 can be formed in the center section 155 of the top surface 112 around the open first end 142 of the needle access channel 140. The fenestrations 160 can be formed in the portion of the top surface 112 that extends between the top opening of the valve compartment 130 and one end of the implantable base 110 near the open first end 142.

In addition, as shown, the fenestrations 160 can be formed as part of the wall structure that defines the needle access channel 140. For example, the fenestrations 160 can be formed along at least a length of the curved bottom section 141 of the needle access channel 140. In one embodiment, both the curved top section and the curved bottom section can include the fenestrations 160. In other words, the fenestrations 160 can be formed along the needle access channel 140.

Metal (Metallic) Foam

As is known, metallic foam is a cellular structure made up of a solid metal containing a large volume fraction of gas-filled pores. These pores can either be sealed (closed-cell foam), or they can be an interconnected network (open-cell foam). Frequently, the metallic foam is formed of a titanium alloy. In the illustrated embodiment, an open-cell metallic foam structure is illustrated in that the implantable base 110 can be formed of metallic foam and have a perforated look. For example, the sides and ends of the implantable base 110 can include through holes that access the hollow interior of the implantable base 110. However, as mentioned, the holes do not pass through the walls of the valve compartment 130.

These network of holes in the implantable base 110 form a 3D printed foam. The metallic foam is a lattice of metal that connects to contain a volume of mostly empty space for tissue ingrowth. The size of the holes and the thickness of the lattice is designed to balance the ease and cost of 3D printing while also optimizing the stability of the implant when tissue-ingrowth has occurred. The outward surfaces of the metallic foam are smooth so that there are no sharp edges when holding the device 100.

It will be appreciated that the other implantable bases disclosed herein can have this same construction.

Movable/Displaceable Valve 200

The device 100 also includes a movable/displaceable valve 200 that is disposed within the valve compartment 130. The valve 200 moves between a closed position or lowered position (FIG. 5) and an open or raised position (FIG. 1). In the closed position, the valve 200 is in its lowered position and closes off (fully obstructs) the needle access channel 140 so that the wound is closed and back-bleeding is prevented. Conversely, in the open position, the valve 200 is in its raised position and the needle access channel 140 is thereby opened to allow passage of the needle 10 through the device 100 to the target vascular site (blood vessel). In its raised position, the valve 200 can extend 1-2 mm above the top surface of the implantable body 110.

The valve 200 comprises a valve body 210 that includes a top surface 212, an opposite bottom surface 214, opposite side surfaces 215, a first end surface 216, and an opposite second end surface 218. The first end surface 216 faces the first end 120 of the implantable body 110 and the second end surface 218 faces the opposite second end 122 of the implantable body 110.

The top surface 212 is preferably a substantially planar surface since it is for placement below the subcutaneous tissue and cannot have any protrusions or features that would impinge or otherwise jab the subcutaneous tissue. Since the bottom surface 214 is designed to face and be located above the target vascular site, the bottom surface 214 can have a slight degree of curvature and be concave in shape.

While the first end surface 216 is generally arcuate shaped, it has a compound shape and is defined by a top section 211 and a bottom section 213. As described in more detail below, the front of the valve body 210 can be shaped to match the taper of the standard dialysis needle 10 so that when the needle 10 is pressed against the front of the valve body 210, the resultant force is to push the valve body 210 to its open (raised) position. In other words, it is configured such that constrained axial movement of the needle within the needle access channel 130 is translated into axial (linear)

movement of the valve body 210 in a direction that is orthogonal to the center axis of the needle access channel 130.

One of the prominent features of the first end surface 216 is a needle contacting section that can be thought of as being a cam surface 219. The cam surface 219 spans from the top section 211 to the bottom section 213.

The cam surface 219 is recessed relative to surrounding sections of the first end surface 216 and can have a circular, oval or oblong, or other shape including irregular shapes. The cam surface 219 can therefore have a concave or angled shape. It is this cam surface 219 that first contacts the distal tip of the needle 10 as the needle 10 travels down the needle access channel 140. The valve body 210 is angled in such a way that the first end surface 216 is angled toward the needle access channel 140 and more particularly, the cam surface 219 can in part define the top surface of the needle access channel 140.

The valve body 210 can also include an angled bottom surface 217 that extends between the bottom section 213 of the first end surface 216 and the bottom surface 214.

Since the cam surface 219 is within the confines of the needle access channel 140 and more particularly, at least a portion of the cam surface 219 lies within the needle access channel 140, the forward progress of the needle 10 within the needle access channel 140 results in the distal tip of the needle 10 contacting the cam surface 219. Moreover, continued forward axial movement of the needle 10 in the needle access channel 140 is translated into axial upward movement of the valve body 210 in the valve compartment 130 in a direction orthogonal to the center axis of the needle access channel 140. It will be appreciated that the concave nature of the cam surface 219 is complementary to the shape (curvature) of the needle 10. In particular, the angling and curvature of the cam surface 219 assists in providing smooth ingress and forward advancement of the needle 10 within the needle access channel 140.

As the needle 10 advances, the needle 10 contacts and lifts the valve body 210 within the valve compartment 130 to its raised (open) position. The needle 10 transitions to and seats against the angled bottom surface 217 and remains in intimate contact with angled bottom surface 217 even after the needle 10 reaches the target vascular site and is held stationary within the needle access channel 140. This angled bottom surface 217 is thus formed to cradle the needle 10 and therefore, the angled bottom surface 217 can have an arcuate shape.

Another aspect of the cam surface 219 and its arrangement and orientation relative to the needle access channel 140 is that the urging action of the needle 10 is not dependent on the orientation of the needle 10. In other words, the taper of the front (first end surface 216) is therefore extended so that is functions correctly regardless of the orientation of the bevel of the needle (for example, if the needle is inserted bevel up or bevel down). Most needles 10 have an angled (beveled) distal tip and regardless of whether the angled wall is facing upward or downward, the needle 10 contacts the cam surface 219 as it advances. This provides a fail-safe in that the operator does not have to insert the needle 10 is a specific orientation in order to cause the valve body 210 to move from the lowered position to the raised position.

The bottom section 213 and the angled bottom surface 217 slopes inward toward the center of the valve body, while the top section 211 is configured closer to a 90 degree angle to the top surface.

A pair of spaced rails or ribs 230 is formed along the first end surface 216 at the two opposing outer edges thereof. The rails 230 are formed parallel to one another and have the same construction so as to impart symmetry. The cam surface 219 is located between the pair of spaced rails 230. The spaced rails 230 are designed as part of the mechanism to ensure that the valve body 210 moves linearly within the valve compartment 130 and does not become completely dislodged from the valve compartment 130. In particular, the since valve compartment 130 is formed at a slant and the valve body 210 moves linearly along this direction that is angled relative to the top and bottom surfaces, the pair of rails 230 contact the first end wall 131 of the valve compartment 130 when the valve body 210 moves to the open (raised) position. In other words, there is an interference fit between the first end wall 131 and the pair of rails 230 as the valve body 210 moves to the deployed (raised) position. This interference fit prevents the valve body 210 from freely popping out of the valve compartment 130 and thus, can be considered to be a type of mechanical stop for limiting the degree of movement of the valve body 210. This relationship is shown in the figures which shows the valve body 210 in the raised position.

The valve body 210 has a bottom seal portion 220 that is configured to seal the bottom opening (open second end 144) of the needle access channel 140 when the movable valve 200 is in the lowered position. The open second end 144 can be thought of as being a bottom opening (exit) of the device 100. The bottom seal portion 220 has an oblong shape and can be defined by an outer beveled section 222 and a center section 224. Both the outer beveled section 222 and the center section 224 have oblong shapes; however, they can equally have other shapes so long as they are complementary to the shapes of the bottom of the valve compartment 130 and the bottom opening of the device 100. The center section 224 can be planar.

The bottom section 139 (floor) of the valve compartment 130 acts as a valve seat when the valve 200 is in the lowered position. More particularly, the outer beveled section 222 of the valve body 210 seats against the bottom section 139 of the valve compartment in a sealed manner. The bottom section 139 can be considered to be a valve seat of the device. Simultaneously, the center section 224 seats within the open second end 144 of the needle access channel 140. The center section 224 thus plugs the open second end 144 and seals it from exterior fluid entry (e.g., back-bleeding). Thus, the combination of the outer beveled section 222 and the center section 224 seals the needle access channel 140. The bottom seal portion 220 closes off the bottom of the implantable body when the valve 200 is in the lowered position. This sealing action effectively closes off and seals the wound and prevents back-bleeding since blood from the pierced vascular structure (blood vessel) cannot flow into the needle access channel 140. Thus, in the lowered (closed) position, the movable valve 200 obstructs and closes off the needle access channel 140 and seals the wound and prevents back-bleeding.

The aforementioned design features thus permit the valve 200 to be constrained in the valve compartment 130 so that the valve 200 moves linearly and orthogonally to the axle of the needle tube, which is the minimum possible distance to clear the needle 10.

In one important aspect, the movable valve 200 operates in a self-sealing manner in that the closing of the movable valve 200 from the raised position to the lowered position, so as to close off the needle access channel 140 and seal the wound, occurs without active input from the person in which the device 100 is implanted. Moreover, no motorized components are provided for moving the valve 200 to its lowered position. In one embodiment, the return force that is required to move the valve 200 back to the lowered position is generated by the subcutaneous tissue. In particular, when the movable valve 200 is mechanically displaced to the raised position by insertion and contact between the needle 10 and the valve 200, the overlying subcutaneous tissue is placed under tension due to the top surface 212 of the valve body 210 being raised above the implantable body 110. This stored tension is then released when the needle 10 is removed from the needle access channel 140, thereby allowing the valve 200 to freely move downward to the lowered position.

With respect to the other sides of the valve body 210, the second end surface 218 can have a convex shape that is complementary to the adjacent end wall of the valve compartment 130. The second end surface 218, which can be considered to be a back of the valve, and the opposing end surface of the valve compartment 130 are oriented to constrain the movement of the valve 200 orthogonal to the direction of the needle 10.

In one embodiment, the side surfaces 215 of the valve body 210 press flat against the containing side walls of the valve compartment 130 (i.e., are not tapered) so as to prevent blood from flowing up around the sides of the valve 200 and up through the valve compartment 130. The sides of the valve body 210 can also be wedge-shaped with respect to the axis of the needle 10 so that the width at the back end (second end surface) of the valve 200 is greater than the width at the front end (first end surface) of the valve body 210. For example, the opposite side surfaces 215 of the valve body 210 can be planar surfaces that are formed non-parallel to one another. This prevents the valve body 210 from rotating within the valve compartment 130 and helps guide the movement of the valve body 210 to remain orthogonal to the movement of the needle 10.

Biasing (Spring) Element 250 and Displaceable Valve 199

Figure 11:
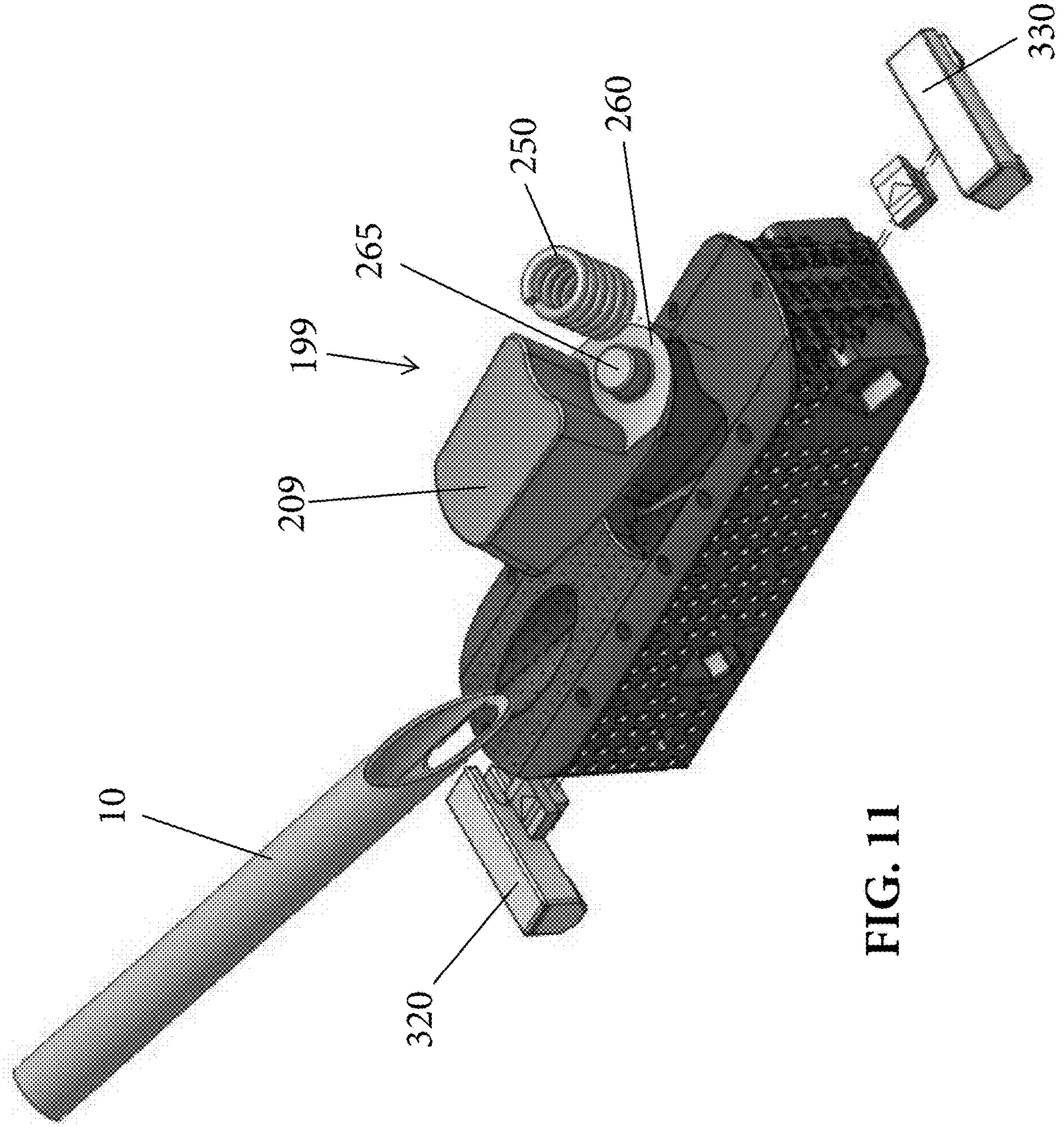
FIG. 11 is an exploded top and side perspective view of a vascular access device in accordance with a second embodiment.
Figure 12:
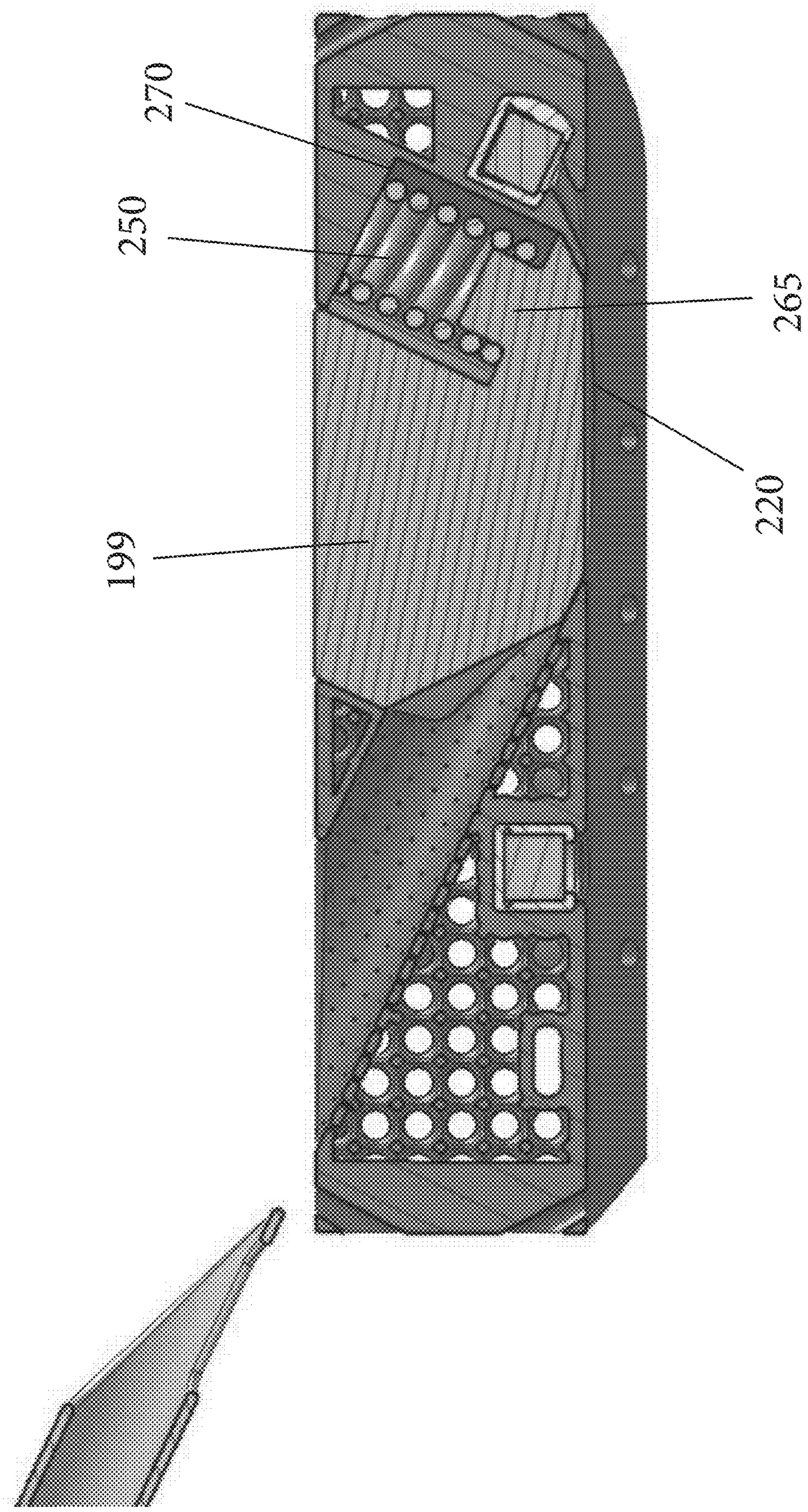
FIG. 12 is a cross-sectional view thereof.
Figure 13:
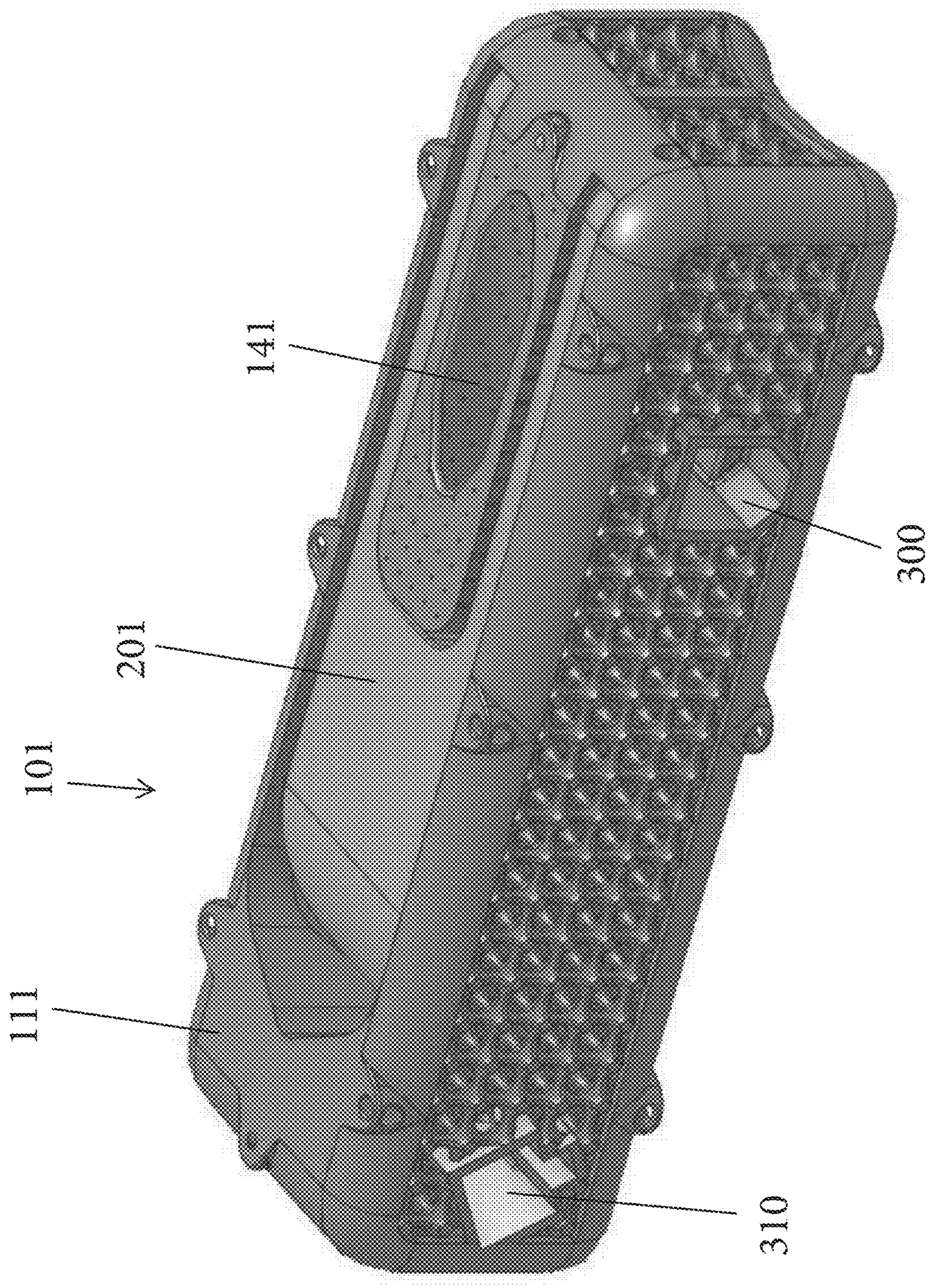
FIG. 13 is an exploded top and side perspective view of a vascular access device in accordance with a third embodiment showing the displaceable valve in the closed position.
Figure 14:
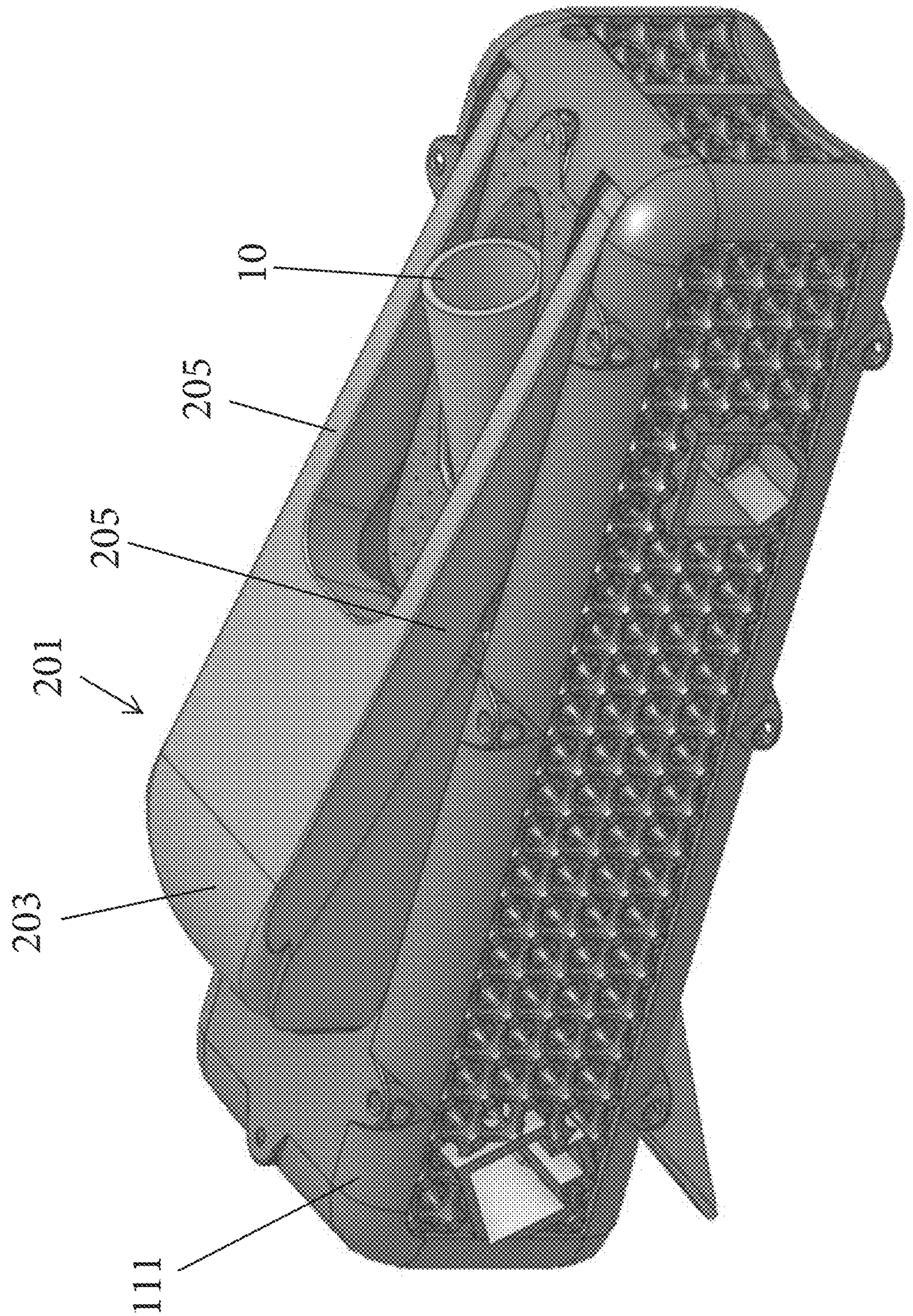
FIG. 14 is a perspective view thereof with the displaceable valve in the open position.
Figure 15:
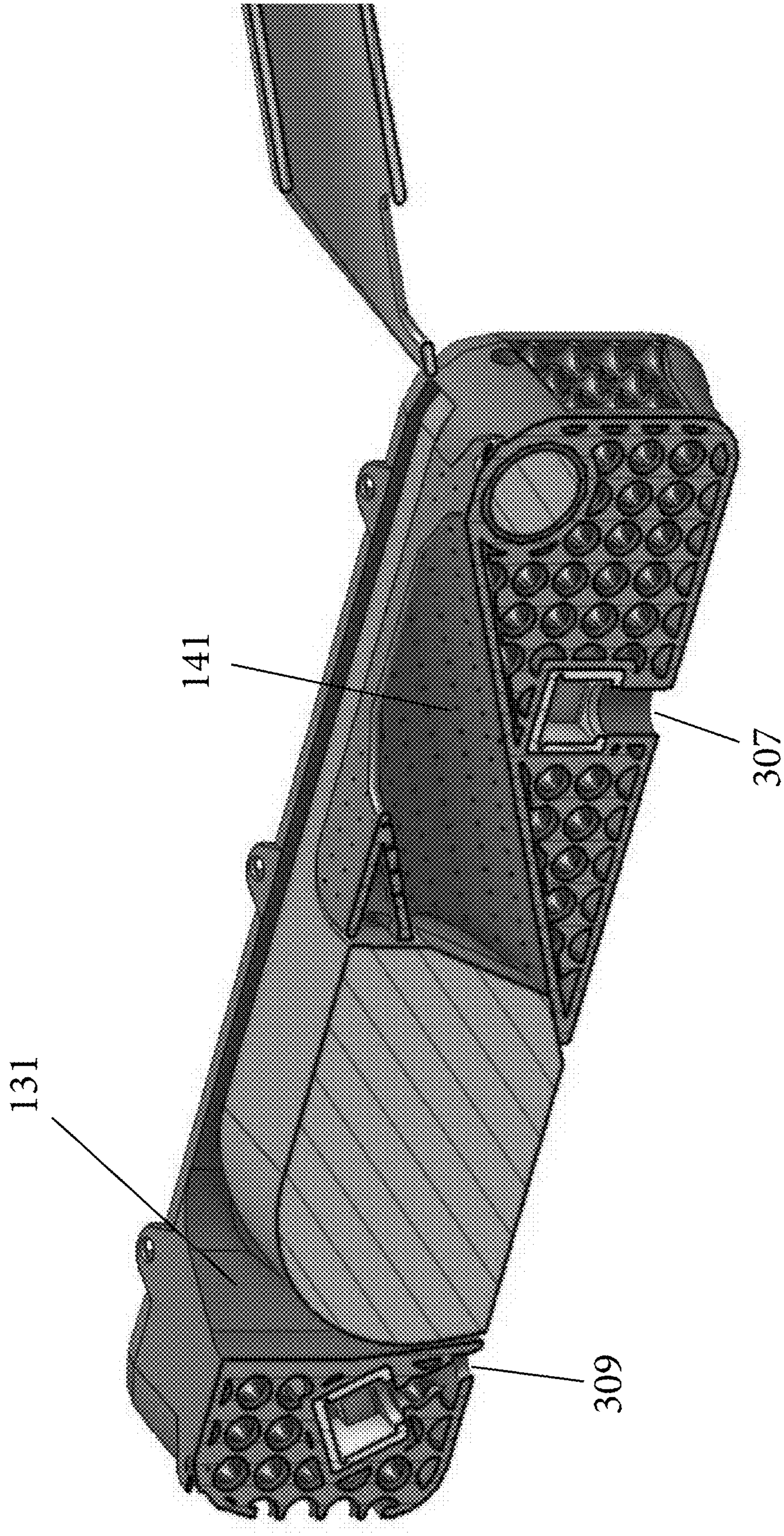
FIG. 15 is a cross-sectional view with the displaceable valve in the closed position.
Figure 16:
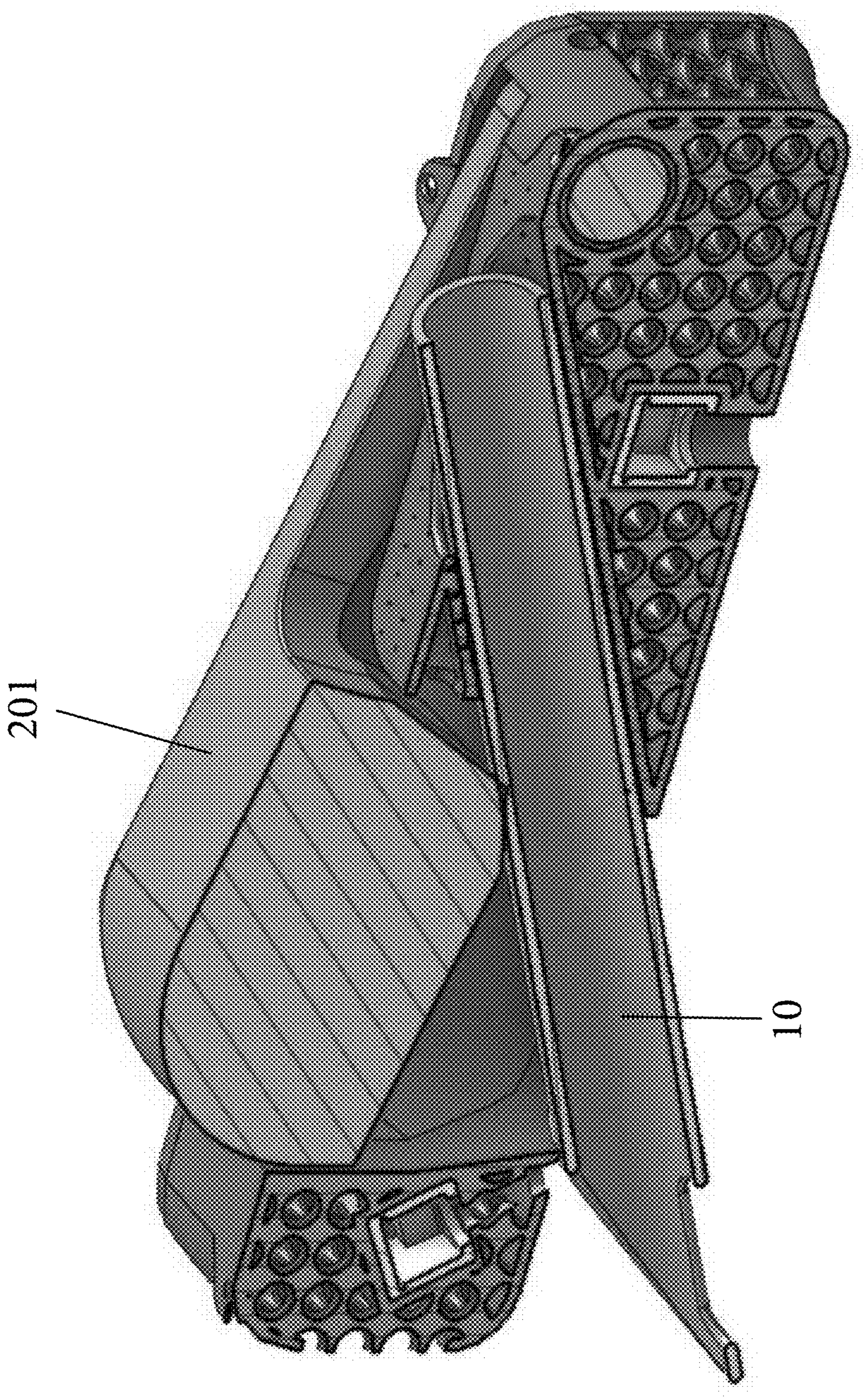
FIG. 16 is a cross-sectional view with the displaceable valve in the open position.

In the embodiment shown in FIG. 11, a biasing element 250 is incorporated to provide a return force to assist a displaceable valve 199 in returning to the closed position after the needle 10 is removed from the needle access channel 140. The valve 199 is very similar in construction to the valve 200 and therefore like elements are numbered alike in the figures.

At the back end of the valve body 210, a retainer or coupling element 260 is provided for coupling the biasing element 250 to the valve body 209. The retainer 260 can be in the form of a rear flange that extends outwardly from the valve body and is located at the bottom of the valve body 209. The rear flange can include a protrusion (a boss) 265 that is intended to contact and engage the biasing element 250 to effectively couple the biasing element 250 to the valve body 209. The rear flange surrounding the protrusion 265 is preferably a flat surface.

For example, the biasing element 250 can be in the form of a coiled (metal) spring having a first end and an opposite second end and the protrusion 265 can have a raised circular shape. This protrusion 265 is received within the second (lower) end of the coiled spring, thereby coupling the coiled spring to the valve body 209. The second end of the coiled spring seats flush against the flat surface of the rear flange that surrounds the protrusion 265. The secure fit between the protrusion 265 and the coiled spring comprises a friction fit. The first (upper) end of the coiled spring seats against a ceiling section 270 of the valve body 209 and more particularly, of the valve compartment 130. Given the orientation of the valve 199 within the valve compartment 130 (i.e., orthogonal to the longitudinal axis of the needle access channel and the needle), this ceiling section 270 is slanted and lies in a plane that is parallel to the longitudinal axis of the needle access channel 130. The ceiling section 270 is flat to allow the first (upper) end of the coiled spring to seat flush thereagainst.

The biasing element 250 applies a return force in that when the valve body 209 is urged upwards to the open position by the driving action of the needle 10, the biasing element 250 stores energy. When the obstruction created by the needle 10 is removed from the needle access channel 130 and the needle 10 clears the valve body 209, the stored energy of the biasing element 250 is released. This released energy is manifested in a downward driving action of the valve body 209 within the valve compartment 130. More specifically, the released energy drives the valve body 209 to the closed position in which the bottom seal portion 220 of the valve body 209 seats against the bottom section of the valve compartment 130 and seals the bottom opening (open second end 144) of the needle access channel 140 in the manner described herein.

It will also be appreciated that the presence of the biasing element 250 also controls and prevents undesired rearward movement of the valve body 209 within the valve compartment 130. The movement of the valve body 209 is thus constrained in the valve compartment 130 and the valve body 209 can only move in a linear direction that is orthogonal to the longitudinal axis of the needle access channel 140 (and the needle 10).

Vascular Access Device 101 Including Hinged Valve 201

In yet another embodiment shown in the FIGS. 13-16, a device 101 that is similar to device 100 is provided with like elements being numbered alike. The main difference between the device 100 and the device 101 is that the device 100 includes a collinear valve that moves linearly within the valve compartment, while the device 101 includes a hinged valve.

A valve compartment 131 in the device 101 is thus configured to receive a hinged valve 201 that is hingedly coupled to an implantable base 111 of the device 101. The valve compartment 131 permits the desired movement of the hinged valve 201 in that the hinged valve 201 can move between an open (raised) position and a lowered (closed) position.

The implantable base 111 is like the implantable base 110 in that it includes a needle access channel 141 that is formed at a fixed angle and it open at both ends along the top and bottom surfaces, respectively, of the implantable base 111. The needle access channel 141 opens into the valve compartment 131. The needle access channel 141 can have the same or similar attributes as the needle access channel 140 and therefore, for sake of brevity, these attributes will not be repeated.

The hinged valve 201 has a main body 203 along with a pair of arms 205 that extend rearwardly from the main body 203. The pair of arms 205 are parallel to one another with an open space formed therebetween. The free ends of the arms 205 are pivotally coupled to one end of the implantable base 111. In this way, the hinged valve 201 can pivot upward about a pivot axis passing through the pivots at the free ends of the pair of the arms 205.

The needle access channel 141 is located between the pair of arms 205 and therefore, remains accessible regardless of whether the hinged valve 201 is in the raised position or the lowered position.

The hinged valve 201 works in the same manner as the valve 200 in that the distal end of the needle 10 contact and drives the hinged valve 201 upward. The hinged valve 201 thus includes a cam surface, the same as or similar to the cam surface 119, that is contacted by the needle 10 and the continued driving of the needle 10 causes pivoting of the hinged valve 201 at the pivot axis near one end of the device 101.

Like the valve 200, an interference fit is formed between the hinged valve 201 and the valve compartment 131 that limits the pivoting range of the hinged valve 201. More specifically, a front end 197 of the hinged valve 201 contacts a front surface of the valve compartment 131 so as to prevent excessive upward pivoting of the hinged valve 201.

It will be understood that the device 101 is a self-sealing device like the device 100 in that the valve 201 returns to its closed position by: 1) the pressure exerted on the top surface of the valve by the subcutaneous tissue; 2) through the force of a biasing element (spring); or 3) by both the pressure differential on the top and bottom surfaces of the valve and the force of the biasing element.

The device 101 like device 100 can be formed of metallic foam and include fenestrations to permit tissue ingrowth.

Internal 3D Printed One Piece Spring Mechanism

In one aspect, the displaceable valve can include an internal 3D printed one piece spring mechanism that is configured to return the valve to the closed position. The spring system can be in the formed of a polymer sheet that abuts the top surface of the valve and is stretched/deformed by the movement of the valve and applies pressure to return the valve to its closed position. In another embodiment, the spring is 3D printed along with the valve itself and the implantable base so that the entire mechanical device is one compliant unit. In this embodiment, the spring is designed to stretch uniformly as the needle enters the device and pushes on the valve. The 3D printed spring is optimized to expand to the correct operational range without permanent deformation.

Dedicated Interior Spaces and Sensor Arrangement

The vascular access devices described herein can include one or more dedicated interior spaces that are accessible along one or more sides of the vascular access device. For example, the vascular access device 100, 101 can include a first dedicated interior space in the form of a first opening or slot 300 and can includes a second dedicated interior space in the form of a second opening or slot 310. In the illustrated embodiment, the first dedicated slot 300 is formed on one side of the needle access channel 140 and the valve compartment 130 and the second dedicated slot 310 is formed on the other side of the needle access channel 140 and the valve compartment 130. In the illustrated embodiment, both the first and second dedicated slots 300, 310 are through holes or through slots in that they pass completely through the implantable base 110, 111 from one side to the other side. In this way, each of the first dedicated slot 300 and the second dedicated slot 310 can be accessed either along the first side or the opposite second side of the implantable base, thereby providing flexibility to the surgeon. The first and second dedicated slots 300, 310 are for receiving external objects, such as electronics.

In one aspect each of the first dedicated slot 300 and the second dedicated slot 310 is keyed to receive an external object (electronic component) in a prescribed orientation so that the external object can only be inserted in one orientation and is prevented from unintended movement within the respective dedicated slot. In order words and more specifically, the first and second dedicated slots 300, 310 are designed so that they the external objects (electronics) cannot be inserted upside-down or mixed-up so that the wrong external object is inserted into the wrong dedicated slot.

As shown in the bottom plan view of the device 100, there is a first bottom opening 307 that is open to the first dedicated slot 300 and a second bottom opening 309 that is open to the second dedicated slot 310.

In one embodiment, the external objects are part of a sensor device (arrangement) that is configured to detect the presence of the needle 10 within the device 100, 101 and transmit (wirelessly) the data to an external receiver (e.g., computing device, etc.). The sensor device can be used to detect that the needle 10 is in the correct place (and the user should stop advancing the needle 10 to protect the back wall of the fistula). In this application, a first sensor component 320 is for insertion into the first dedicated slot 300 and a second sensor component 330 is formed insertion into the second dedicated slot 310. The first dedicated slot 300 can be a light source housing and the first sensor component 320 can be a light source, such as an LED unit. The second dedicated slot 310 can be a sensor housing and the second sensor component 330 can be a sensor, such as a light detector or light sensor. As shown, each of the first sensor component 320 and the second sensor component 330 can be in the form of a snap-fitting structure that slides into the respective dedicated slot (from either side of the implantable base) and then snap-fitting locks in place within the implantable base. This slide and lock arrangement ensures that the sensor components are in the proper positions within the implantable base 110. The surgeon can simply remove the sensor components from sterile packaging and then slide then into the dedicated slots until auditory and tactile feedback confirm that the sensor components are locked in place.

In contrast to conventional sensor placement, the first and second dedicated slots 300, 310 are purposely located near the bottom of the implantable base 110, 111. The first bottom opening 307 allows light emitted from the first sensor component 320 to exit the device and pass through the underlying blood vessel for purposes of detecting needle position as well as monitors fistula health. The sensor components 310, 320 described herein can detect changes in blood flow which is a precursor to blockages. The second bottom opening 309 permits scattered light to be received and detected by the second sensor component 330.

The light source within the first dedicated slot 300 emits light in a direction that interests the underlying blood vessel and scattered light is detected by the second sensor component 330. It will be appreciated that different signal patterns are recorded depending upon whether the needle 10 is inserted into the blood vessel or not. For example, prior to insertion of the needle 10 into the device 100, a strong signal is recorded at the second sensor component 330 since the emitted light passes through the blood vessel and is detected by the second sensor component 330. Conversely, when the needle 10 exits the second (bottom) end 144 of the needle access channel 140 and enters the blood vessel, the mass of the device 100 blocks the path of light to the second sensor component 330. The resulting reduction in light can act as a signal to the user that the needle 10 is in the correct place (and the user should stop advancing the needle 10 to protect the back wall of the fistula).

It will be appreciated that there can be a separate device that contains the components necessary to activate the sensor device. For example, a main unit can contain a power source (battery); microprocessor, and transmitter (e.g., Bluetooth antennae(s)). This main unit is likewise implanted under the skin and can be coupled to the device 100 and/or coupled to sensor components 320, 330. An external device, such as a computing device, receives the transmitted signals from the sensor device and processes said signals and provides the desired feedback to the user. For example, the user can launch an app on a smart device or tablet that "wakes up" the sensor device prior to insertion of the needle 10. The activated sensor device then detects the insertion of the needle tip into the blood vessel and an alert (visual and/or auditory) can be given to the user. This alert informs the user to stop advancing the needle ensuring that the needle is in the proper location each time without professional assistance.

The second sensor component 330 is purposely positioned to optimize detection of the scattered light. As shown in the figures, the second dedicated slot 320 is formed at an angle relative to a horizontal ground plane. In other words, the second dedicated slot 320 is slanted with a bottom (floor) of the second dedicated slot 320 being angled to allow more optimal reception of the reflected light. The second sensor component 330 thus does not face directly downward but rather is positioned on a slope relative to the ground plane. In particular, the emitted angle of the light is known as well as the location of the underlying blood vessel and therefore by rotating the second dedicated slot 320 so that is does not face directly downward but instead is at an angle (other than 90 degrees) facing the blood vessel, the scattered light is more optimally collected at the second sensor component 310.

The implantable body 110 can include other openings formed therein. For example, the implantable body 110 can include a transverse hole 340 that is a bounded through hole formed in the implantable body 110. The transverse hole 340 passes completely through the body 110 and is open on both opposing sides of the implantable body 110. The transverse hole 340 can be formed to have any number of different shapes and/or sizes and can be formed in different locations. For example, the transverse hole 340 can be formed below the needle access channel 140 near the bottom of the implantable base.

It will be appreciated that the metallic foam, the fenestrations 160, the dedicated slots 310, 320 for the sensor, the suture holes 20 and the transverse slot 340 help surgeons superficialize the fistula as all slots are visible.

Needle Handle 400

Figure 5:
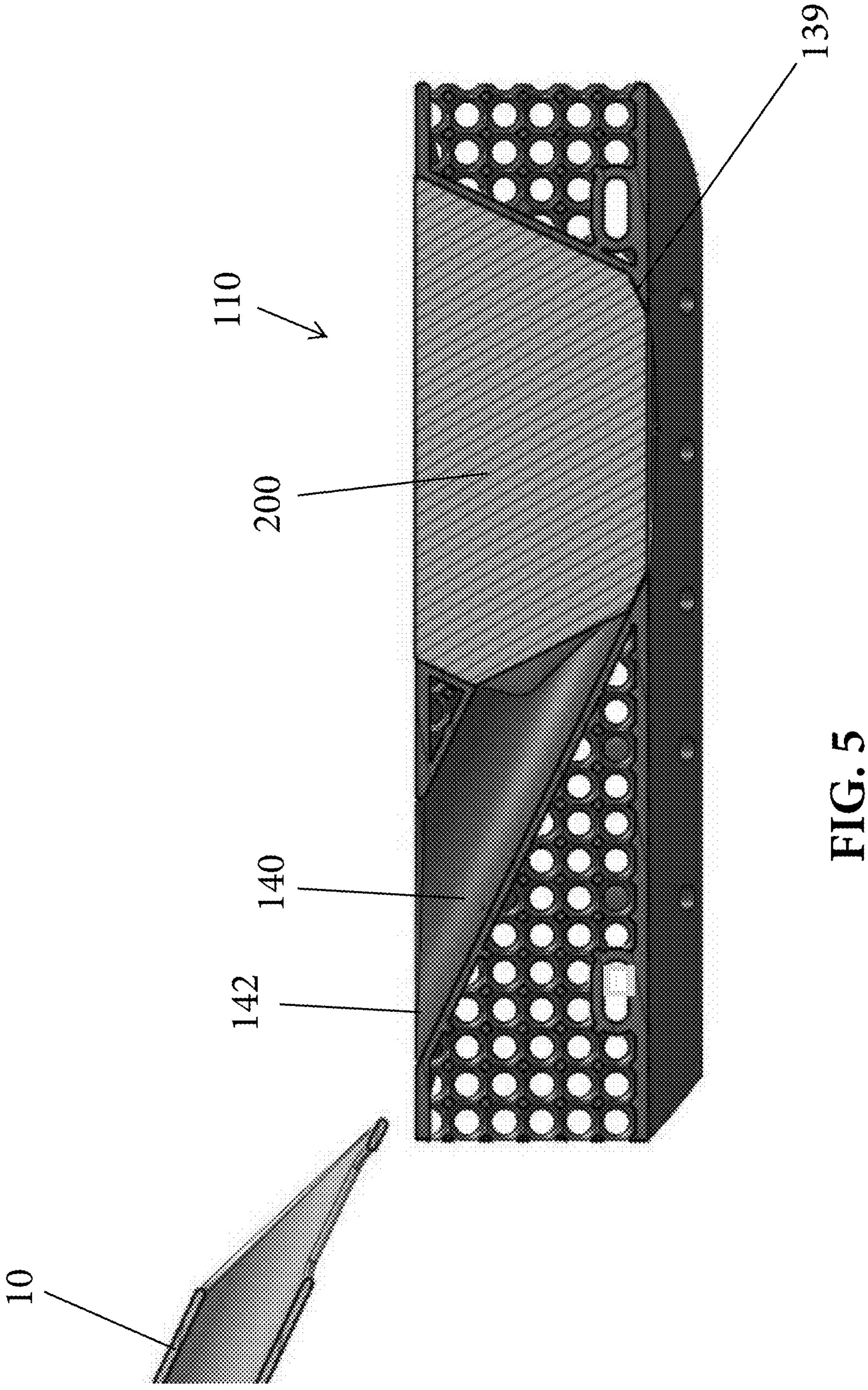
FIG. 5 is another cross-sectional view thereof showing the displaceable valve in a lowered (closed) position.
Figure 6:
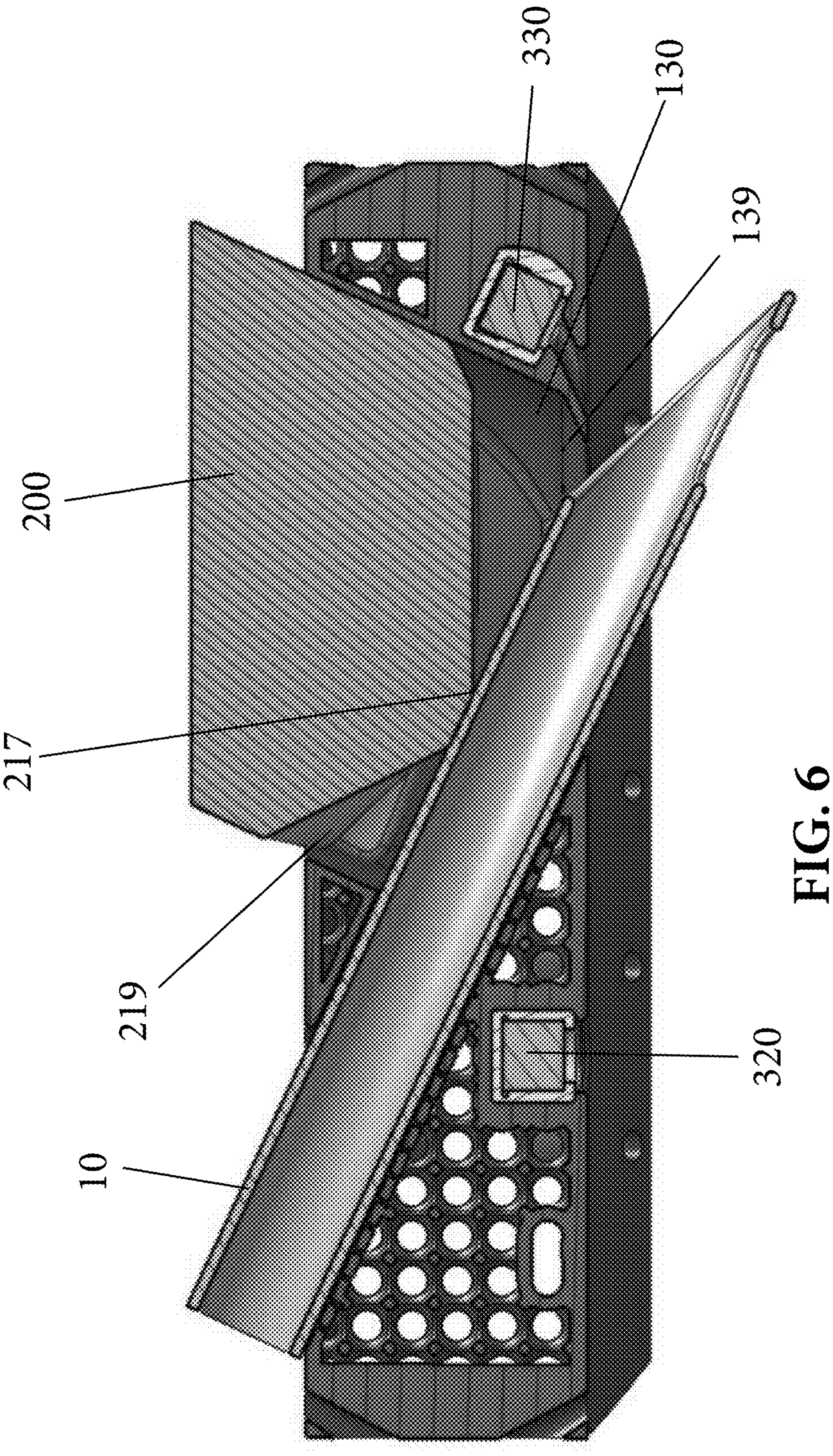
FIG. 6 is another cross-sectional view thereof showing the displaceable valve in a raised (open) position.
Figure 7:
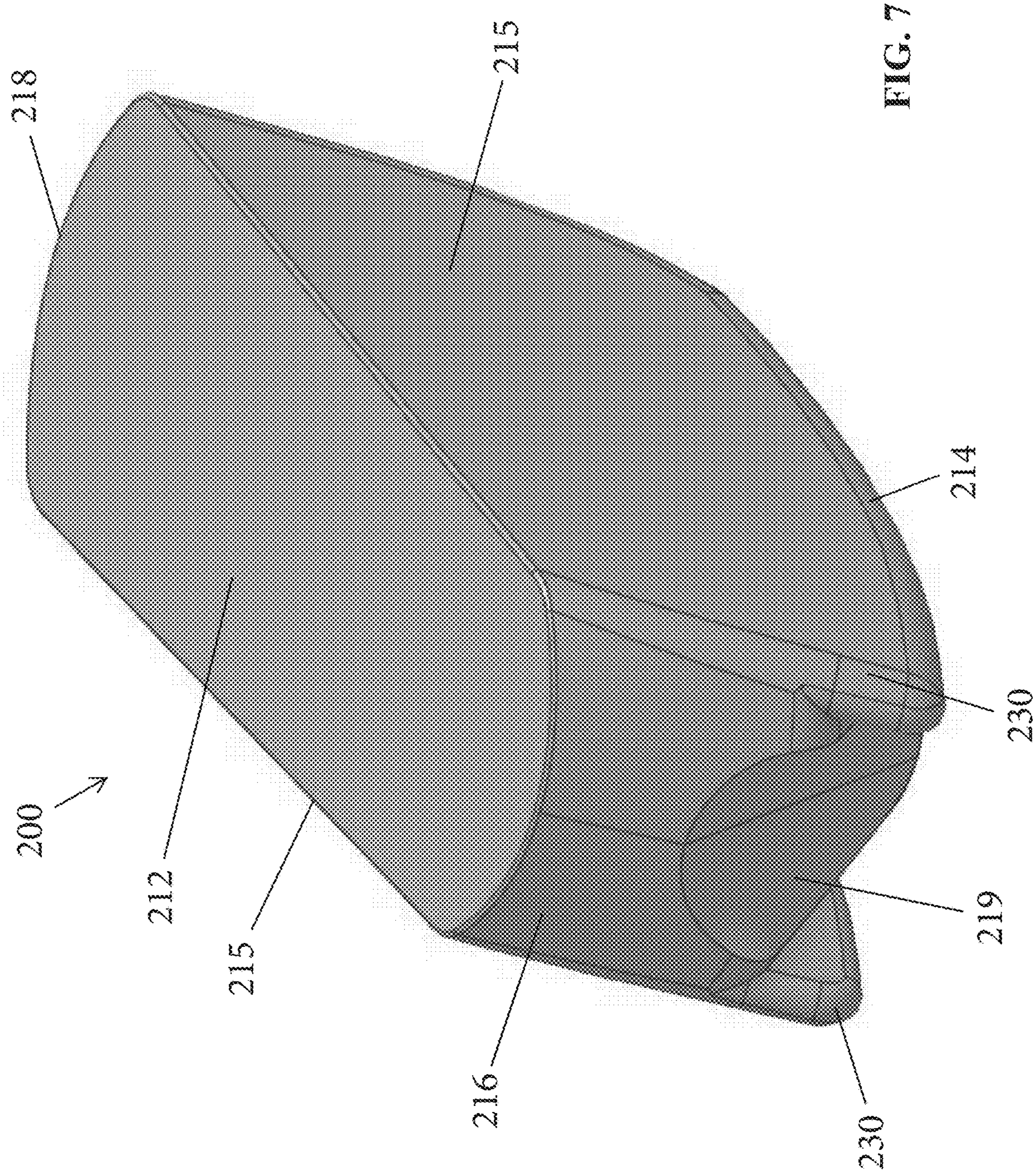
FIG. 7 is a side and end perspective view of the displaceable valve.
Figure 8:
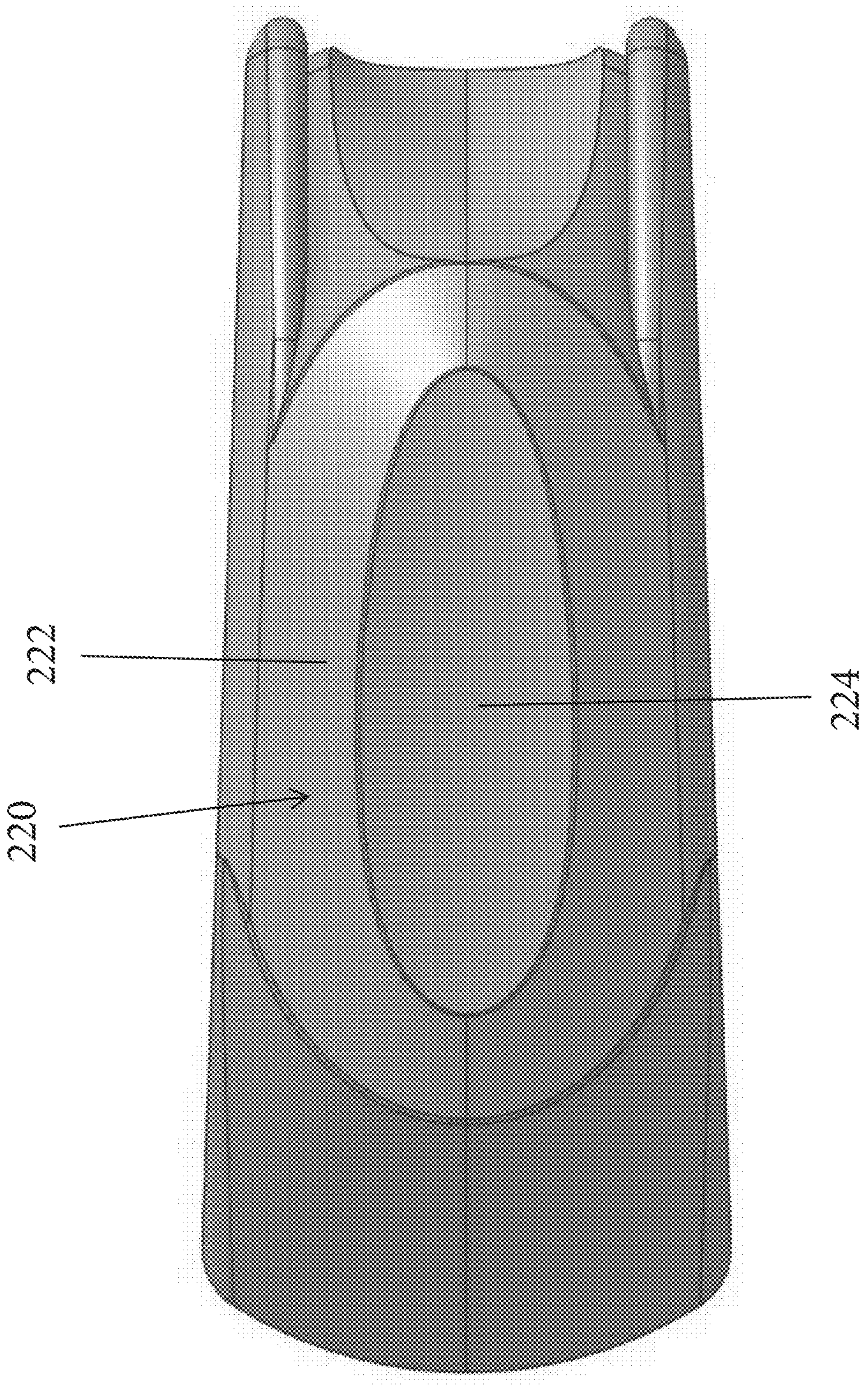
FIG. 8 is a bottom plan view of the displaceable valve.
Figure 9:
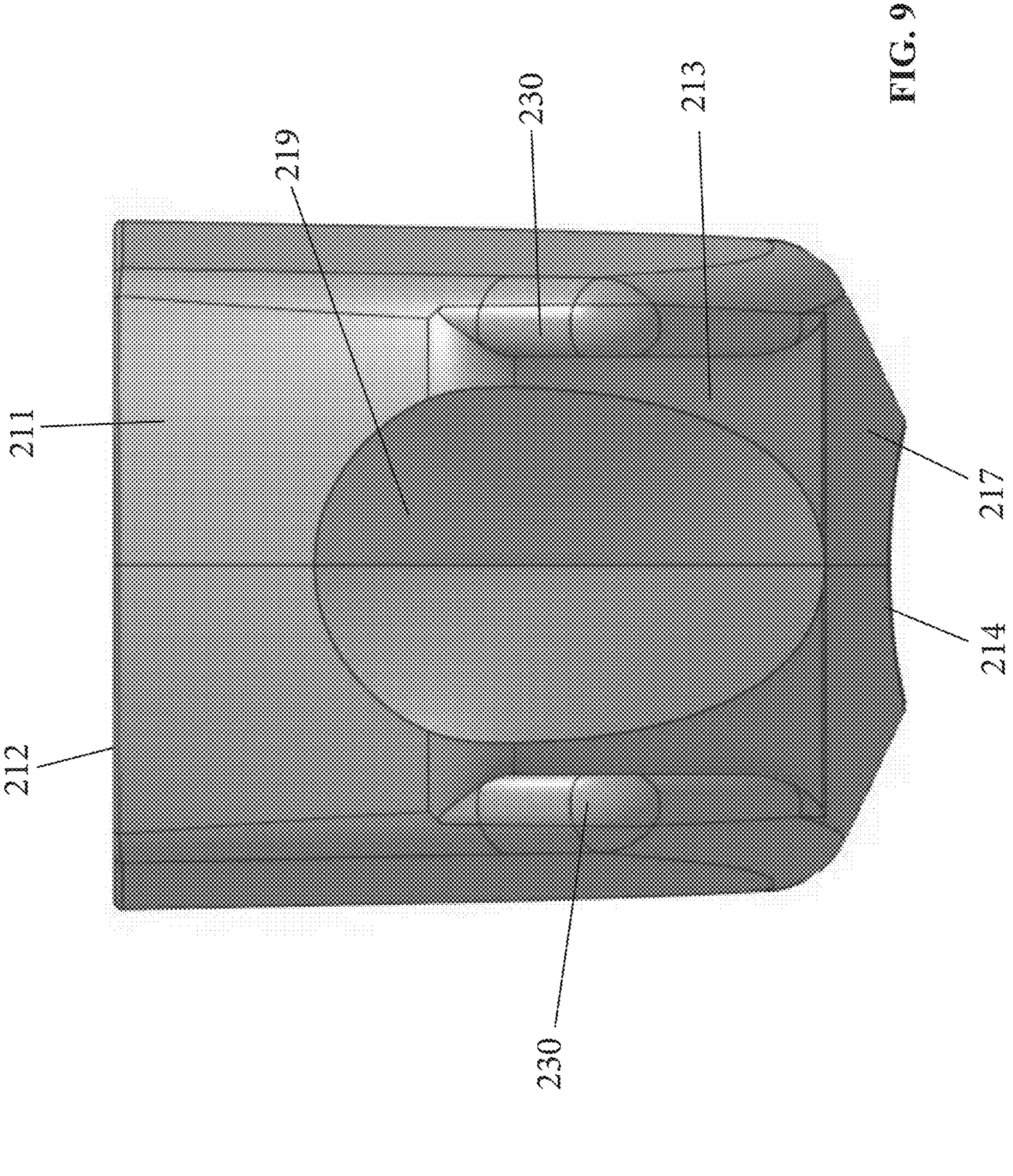
FIG. 9 is an end view of the displaceable valve.
Figure 10:
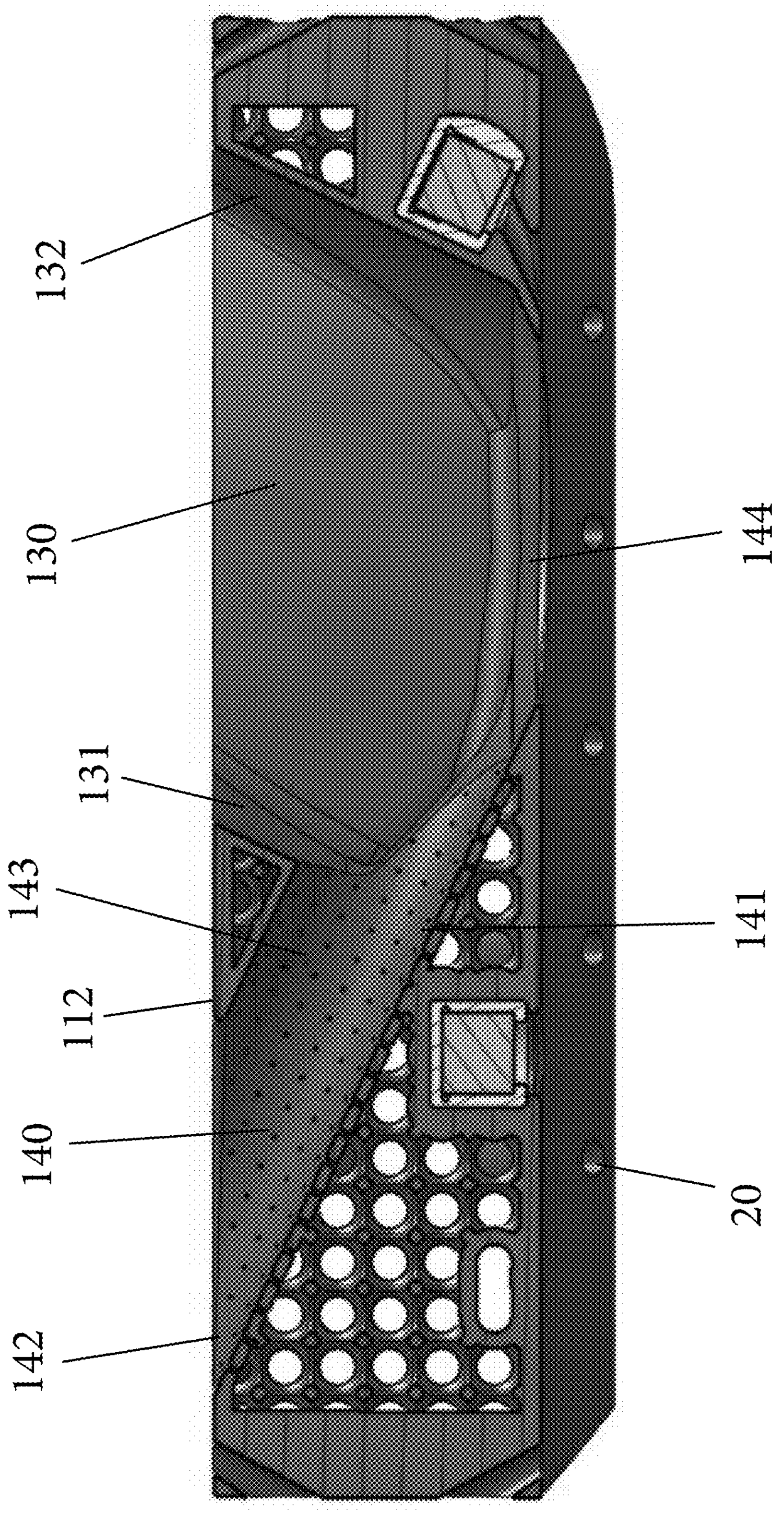
FIG. 10 is another cross-sectional view.
Figure 19:
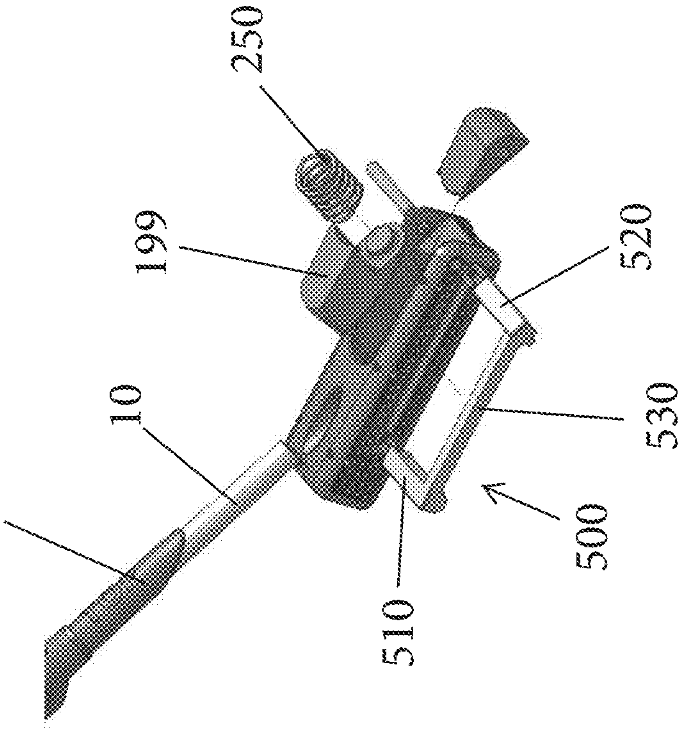
FIG. 19 is an exploded perspective view of one vascular access device with a sensor assembly.
Figure 21:
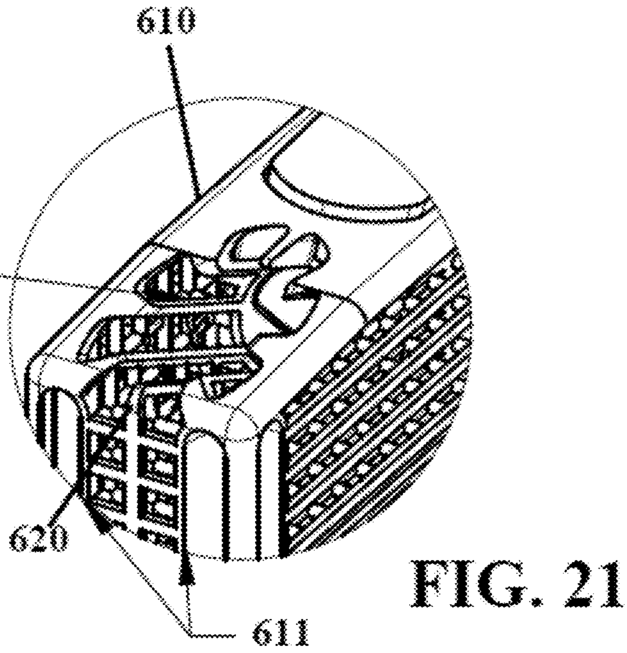
FIG. 21 is an enlarged area taken from FIG. 20.

FIG. 19 illustrates an optional needle handle 400 that is coupled to a proximal end of the needle 10. The needle handle 400 not only provide an ergonomic area for the user to grasp the needle 10 but also acts as a stop limiting the insertion depth of the needle 10 in the needle receiving channel 140. The needle handle 400 is oversized relative to the needle body and therefore it cannot physically enter the open first end 142 of the needle access channel 140. The location of the needle handle 400 is purposely planned so that when the distal end of the needle handle 400 contacts the top surface 112 of the implantable body 110, the sharp (or blunted) distal end (beveled end) extends the prescribed distance below the implantable body 110 (FIGS. 1 and 5).

The distal end of the needle handle 400 can be angled as shown to complement the angle of the needle access channel 140. As a result, when the needle 10 is fully inserted to the desired depth, the angled distal end of the needle handle 400 seats flush against the top surface 112 of the implantable base 110.

The needle handle 400 is thus an easy yet effective way to position the needle 10 at the desired depth and not damage the underlying blood vessel.

Integrated Sensor Assembly 500

In FIG. 19, an integrated sensor assembly 500 is illustrated. The integrated sensor assembly 500 includes both a first sensor component 510 and a second sensor component 520 that is connected to the first sensor component 510. The first sensor component 510 can be the same as or similar to the first sensor component 320 and the second sensor component 520 can be the same as or similar to the second sensor component 330. As a result, the first and second sensor components 510, 520 slide into the first dedicated slot 500 and the second dedicated slot 510. The bridge 530 has a selected length such that the first and second sensor components 510, 520 align with the first dedicated slot 500 and the second dedicated slot 510 and can be inserted therein in a single action.

The external or internal electronics including the main implanted unit and cables (wires) are not shown. However, there can be a single wired connection along the length of the bridge 530 as opposed to having two separate wires.

By connecting the first and second sensor components 510, 520 into one unit that can snap-fittingly lock in place provides for better circuit and cord management, less possibility of error, and easier installation. There is no guesswork in terms of insertion directions of the first and second sensor components 510, 520 since the bridge 530 fixes their relative positions.

Multiple Vascular Access Devices

Figure 17:
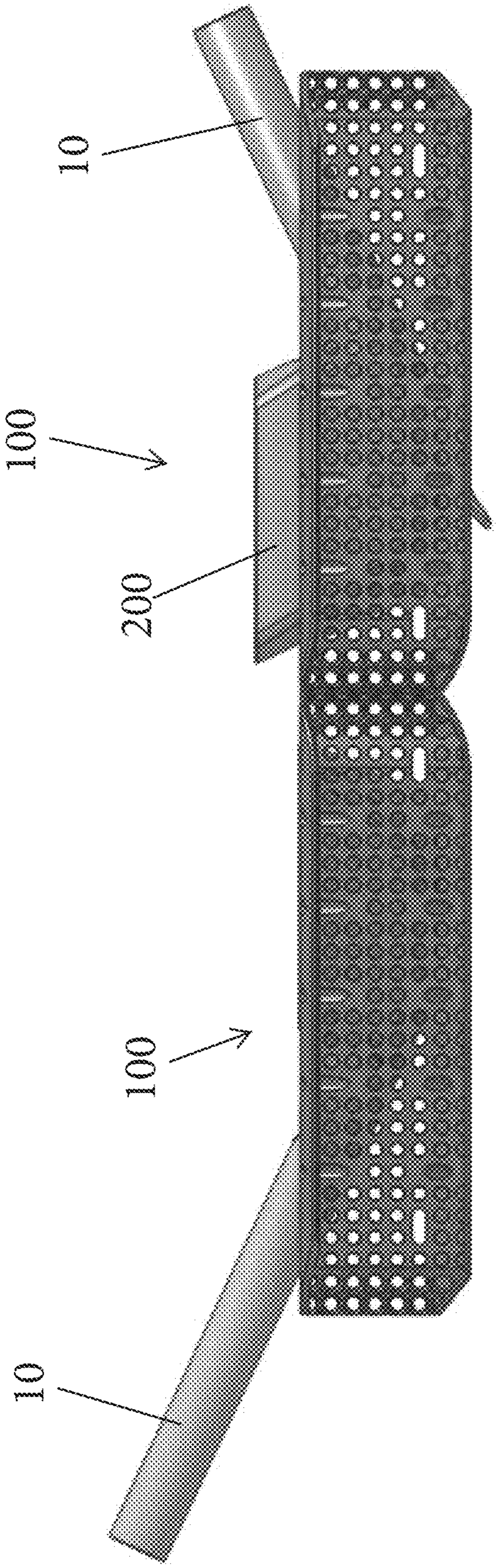
FIG. 17 is a side elevation view of an array of vascular access devices.
Figure 18:
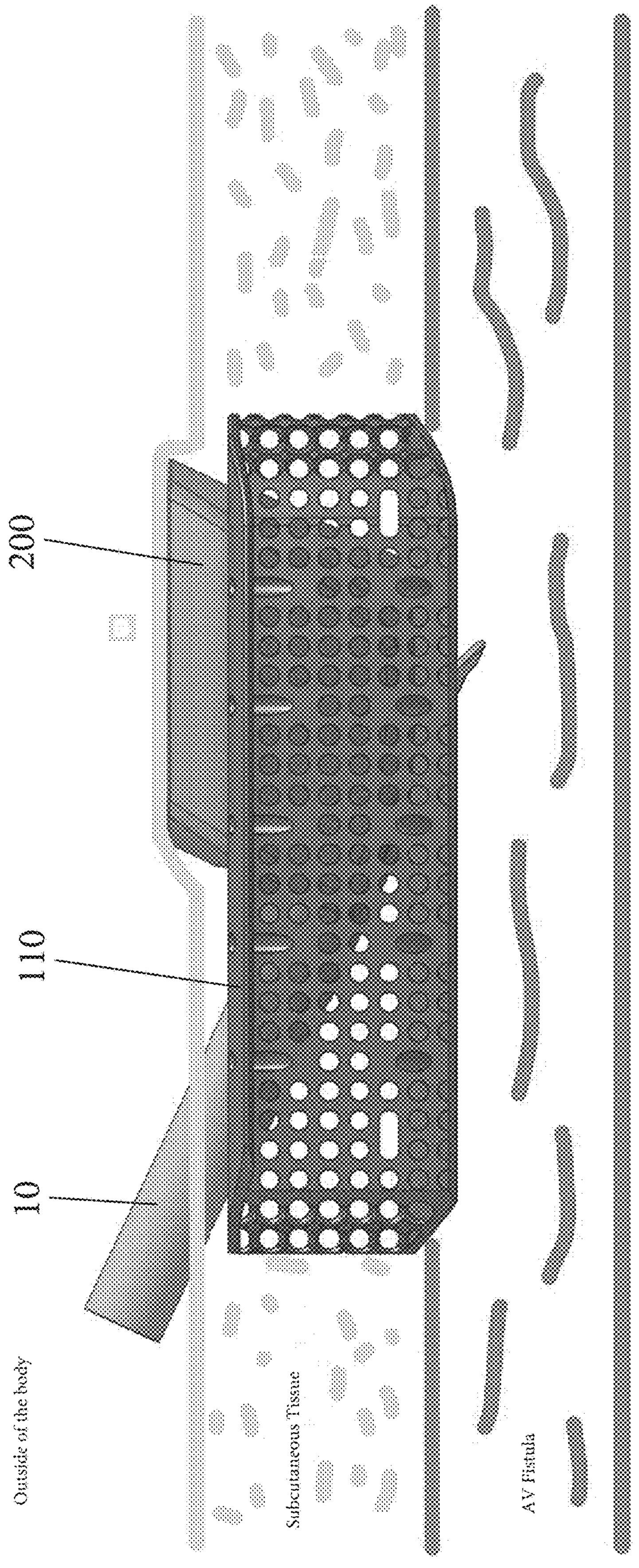
FIG. 18 is a side view showing one vascular access device in an exemplary application above a blood vessel that makes up the arteriovenous (AV) fistula.

As shown in FIG. 17, in certain applications, more than one vascular access device can be used. For example, hemodialysis requires that two dialysis needles be inserted into the patient's vascular access so that blood can flow from the body to the dialysis machine to be cleaned and then back into the body again. As a result, two vascular access devices (e.g., vascular access devices 100) can be positioned in an end-to-end relationship as illustrated. By positioning the second ends 114 of the implantable bases 110 adjacent or facing one another, the two needle entrances into the respective needle access channels 140 are spaced apart from one another.

Vascular Access Device 600

Now turning to FIGS. 20-25, in which a vascular access device 600 according to another embodiment is shown. The device 600 is similar to the other devices described herein and therefore, like components are numbered alike.

The device 600, as well as the other devices disclosed herein, can be coated with silver-added titanium nitride. The coating serves two purposes: (1) further minimizes the already unlikely possibility of metal degradation (i.e., chipping) during repeated cannulations via needle 10 (stainless steel dialysis needle)(titanium nitride has Vickers hardness that is an order of magnitude higher than stainless steel); and (2) significantly reduces chances of biofilm formation as it reduces topographical heterogeneity and as both titanium nitride and silver have been shown to prevent biofilm formation due to their antimicrobial properties.

As described below, the device 600 can be a non-biased device in one embodiment and in another embodiment, the device is a biased device that includes a spring element for biasing the displaceable valve. It will be appreciated and understood based on the following discussion that the device 600 can have modular characteristics in that the same parts can be used to provide different versions of the device with different functionality such as biasing or non-biasing.

The device 600 comprises an implantable base 610 that has a top surface, an opposite bottom surface, a first side, an opposite second side, a first end and an opposite second end. When implanted, the top surface faces the skin (subcutaneous tissue) of the patient and the bottom surface faces the target vascular structure (e.g., blood vessel that makes up the AV fistula). As with the other devices, the vascular access device 600 is configured to controllably deliver the cannula or needle 10 to a target site. As in the other embodiments and described below in more detail, the base 610 can be a largely perforated structure (e.g., metallic foam) in that the sides and ends have openings (through holes) that promote tissue ingrowth. The illustrated structure thus has a grid or mesh like appearance.

The implantable base 610 also includes several internal features such as a valve compartment and a needle access channel. The needle access channel is formed at a fixed angle within the implantable base 610 to allow the needle 10 to be inserted into the blood vessel at a desired angle.

Figure 24:
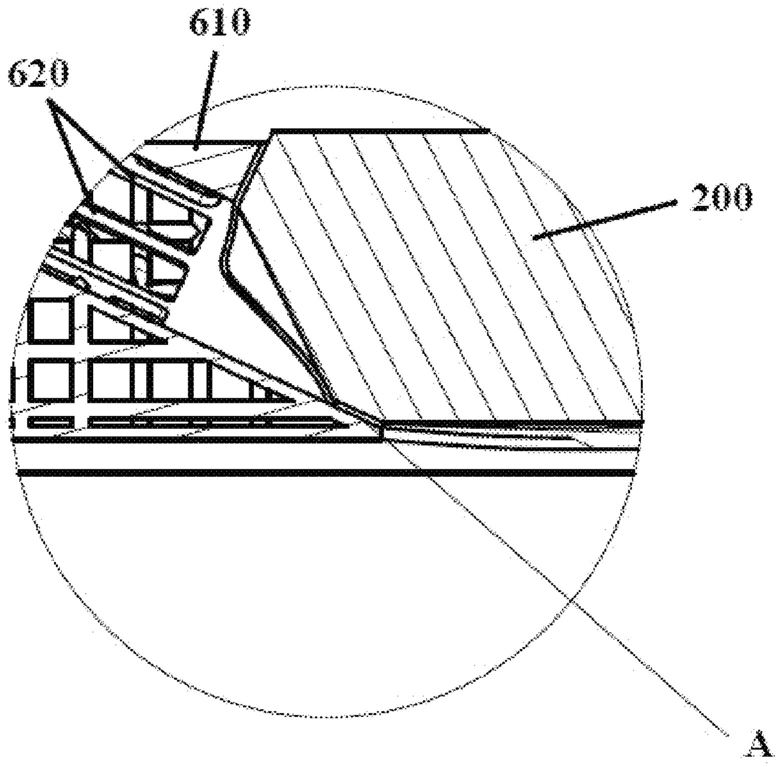
FIG. 24 is an enlarged area taken from FIG. 23.
Figure 25:
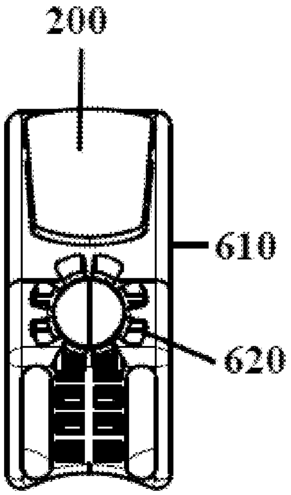
FIG. 25 is a top angled view showing a needle perspective.

As shown in FIGS. 20-25, the needle access channel is defined by a plurality of needle guide rails 620 that are arranged in a circumferential manner to define a needle channel that receives and permits travel of the needle 10. FIG. 25 which is a needle perspective view in that this view shows the entrance into the needle access channel and shows the circumferential pattern of the needle guide rails and the open spacing between them. As in the other embodiments, this entrance is located along the top surface of the base 610 and the needle access channel slopes downward. At the top surface, the needle guide rails 620 remain separated; however, at the bottom region of the needle access channel, the needle guide rails 620 join at a solid structure that guides the needle into the valve compartment.

Each needle guide rail 620 can be in the form of an elongated structure and the needle guide rails 620 are spaced apart from one another and not in contact with one another at least along substantial lengths thereof. In other words, open spaces are formed between the needle guide rails 620 for tissue ingrowth.

The needle guide rails 620 thus define a skeletal framework and the needle guide rails 620 are intended to be covered (completely) by the host tissue, forming an organic buttonhole within the base 610. As described herein, the base 610 can comprise a metallic matrix core. This arrangement prevents exposure of bare metal anywhere in the housing unit, minimizing infection and biofilm formation.

The base 610 which is preferably formed of metallic foam, including the guide rails 620 that form the skeletal backbone of the entrance, has open spacing of about 700 micrometers between solid titanium posts/rails. These are the spacings that will be invaded by the host tissue to form the organic buttonhole. This tissue encapsulation will enable rigid affixation of the device which will prevent dislocation of the needle guide and easy localization through the skin (as it will be a rigid structure).

Figure 20:
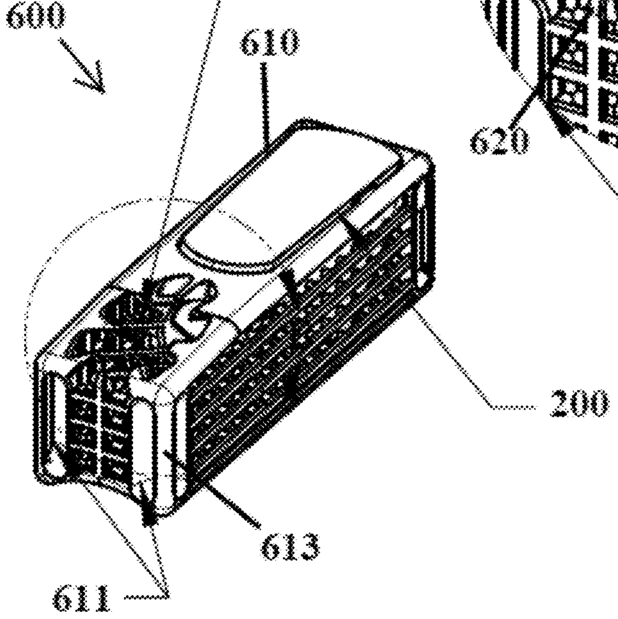
FIG. 20 is an end and side perspective view of a vascular access device in accordance with a third embodiment.
Figure 22:
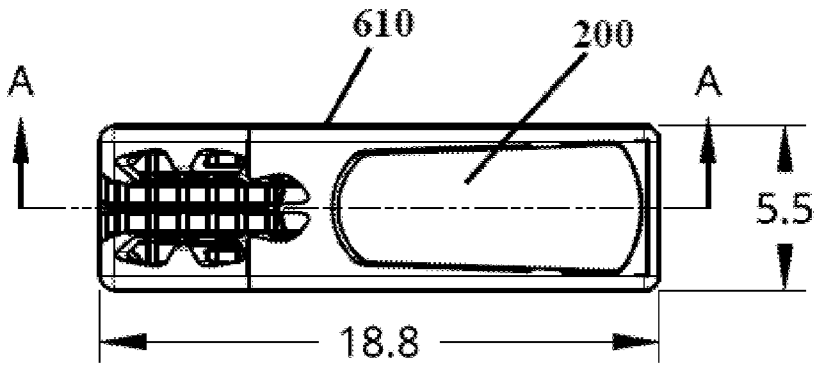
FIG. 22 is a top plan view thereof.
Figure 23:
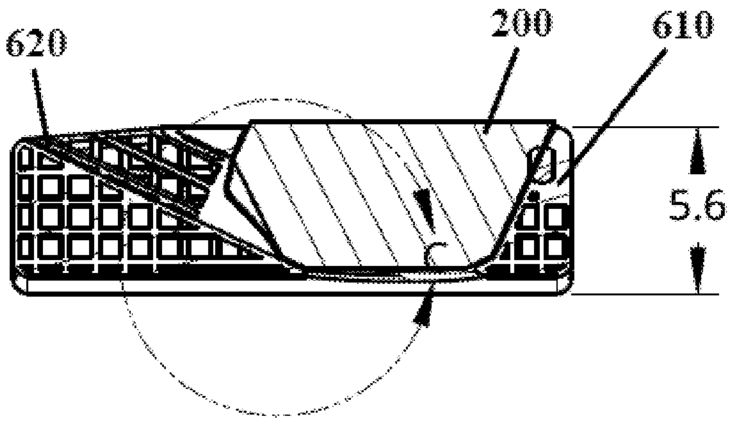
FIG. 23 is a cross-sectional view taken along the line A-A of FIG. 22.

Whereas the previous embodiments has suture holes in the base 610, the embodiment in FIG. 20 has dedicated suture slots 611 in the corners of the base 610. Each suture slot 611 is defined by a vertical support 613 that resembles a handlebar with the suture slot 611 being located behind the vertical support 613. These suture slots 611 allow rapid and free-formed attachment of the device to the subcutaneous tissue as well as the skin and the fistula maximizing surgical flexibility. The base wall behind the vertical support 613 can have a curved shape as shown and thus, the slot can be considered to have a curved shape.

FIGS. 20-25 shows displaceable valve 200 in the closed (lowered) position. In the embodiment of FIGS. 20-25, the displaceable valve 200 is not biased by a biasing element, such as a spring.

In FIG. 24, the reference character A indicates the location at which the valve 200 seats with the housing (base 610) to prevent back-bleeding when the valve 200 is closed. This feature has been described with reference to earlier embodiments.

Figure 26:
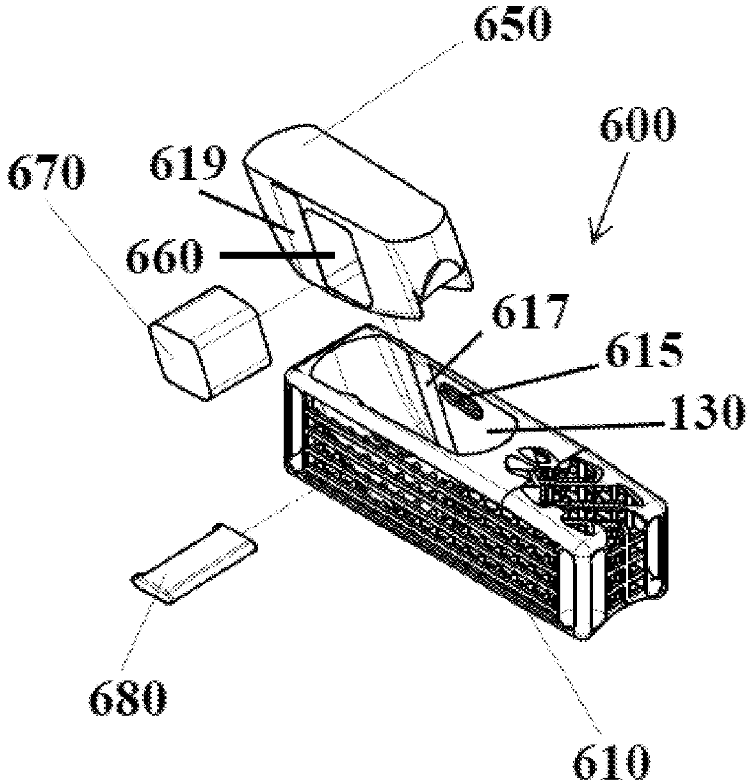
FIG. 26 is an exploded perspective view a vascular access device in accordance with a fourth embodiment.
Figure 27:
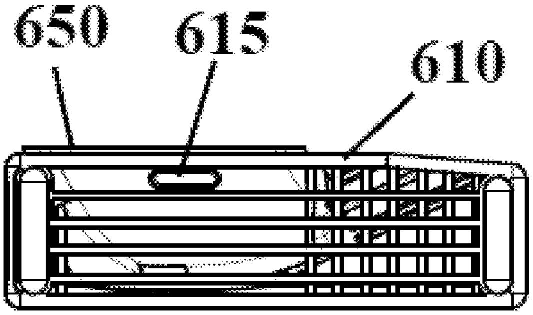
FIG. 27 is side elevation view thereof.

FIGS. 26-32 illustrate the device 600 being used with a biased displaceable valve 650. It will be appreciated that the base 610, with some slight modification, can be used with the valve 650. As shown in FIG. 27, the opposing sides of the base 610 can include opposing slots 615. The slots 615 are formed near the top edges of the opposing sides of the base 610 and can take different shapes and sizes. The illustrated slots 615 are oblong or pill shaped or rectangular shaped. The slots 615 open into the valve compartment in which the displaceable valve is located.

FIG. 26 also illustrates that the base 610 can include a pair of opposing guide ribs 617 (protrusions) that are located internally within the valve compartment 130 and formed along the inner surfaces of the opposing side walls of the base 610. In the illustrated embodiment, the guide ribs 617 can be in the form of curved (convex) ribs. The guide ribs 617 are complementary to guide slots or notches 619 that are formed along the sides of the displaceable valve 650. The guide slots 619 can thus can the form of concave slots. When the displaceable valve 650 is inserted into the valve compartment, the guide ribs 617 are received within the guide slots 619. Receipt of the guide ribs 617 into the guide slots 619 serves to locate and guide the movement of the valve 650 and prevents undesired movements, such as torsional movement. It will be appreciated that the opposite can be true in the guide ribs can be formed along the base and the inner walls of the base can include guide slots.

As mentioned, the displaceable valve 650 is a biased valve and includes a cutout 660 that is formed therein and passes completely through the valve body from one side to the opposing side. The cutout 660 is thus open along the opposing sides. The cutout 660 receives a spring (biasing) element 670 that can be formed of a polymer material. For example, the spring element 670 can be a polydimethylsilaxane (PDMS) elastomeric spring that is inserted into the cutout 660. The PDMS spring element 670 can thus generally take the form of rectangle of biocompatible polymer that is highly resilient to compression. The cutout 660 is defined by a top wall and an opposing bottom wall with the spring element 670 being disposed on the bottom wall. In this embodiment, the spring element 670 is more centrally located within the valve and this provided improved balance and movement of the valve during opening and closing action.

Figure 28:
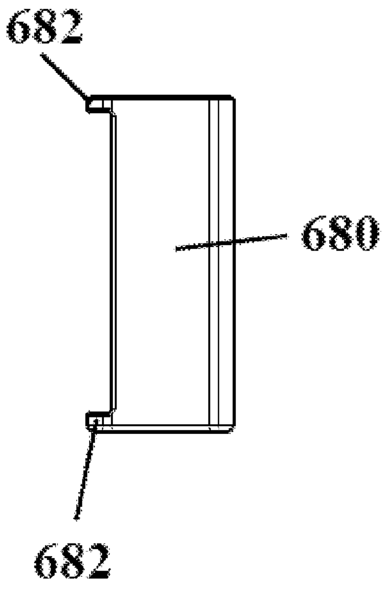
FIG. 28 is a top plan view of a locking pin.

The displaceable valve 650 also includes a locking pin 680. FIG. 28 illustrates the locking pin 680. The locking pin 680 is formed to be complementary to the slots 615 and be disposed within the top section of the cutout 660 above the spring element 670. The locking pin 680 is an elongated structure that can have an oblong or rectangular cross-sectional shape and at the ends of the locking pin 680 there are two tabs 682 with a notch formed between the two tabs along the length of the locking pin. The locking pin 680 is designed to press-fit into position. The tabs 682 act as a failsafe in that the locking pin 680 is inserted through the slots 615 and then pushed backwards (away from the needle) so that the tabs 682 can hook into the sides of the housing (base 610), preventing the locking pin 660 from sliding back out. The forces of the needle and the spring element always act to keep the tabs 682 engaged with the outer surface of the side walls of the base.

The displaceable valve 650 is assembled in the following manner. The spring element 670 is inserted into the cutout 660 of the valve 650. The spring/valve assembly is inserted into the valve compartment of the housing (base 610). The locking pin 680 is inserted through the slots 615 carefully passing over the top of the spring element 670 as it makes the way through the cutout 660.

Figure 29:
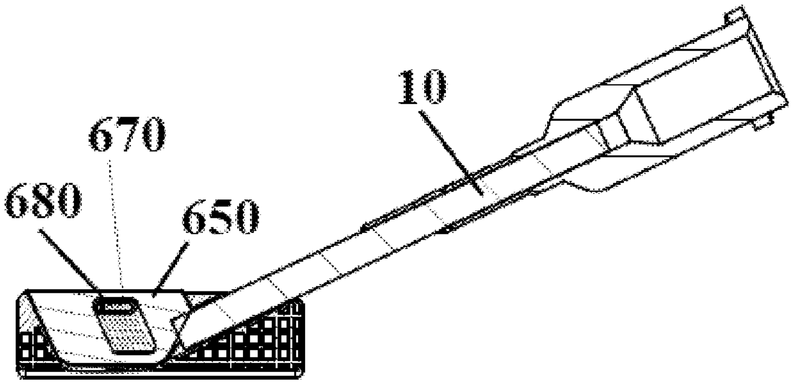
FIG. 29 is a cross-sectional view of the device of FIG. 26 showing a biased displaceable valve in a closed position.
Figure 30:
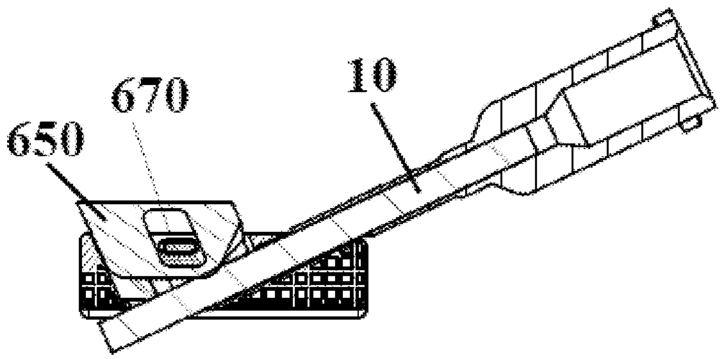
FIG. 30 is a cross-sectional view of the device of FIG. 26 showing the biased displaceable valve in an open position.

FIG. 29 shows the device 600 with the displaceable valve 650 in the closed position and thus, the spring element 670 is not compressed (is in a rest state and not storing energy). This position reflects that the needle 10 has not yet contacted and driven the valve 650 to the open position. FIG. 30 shows the device 600 with the displaceable valve 650 in the open position and thus, the spring element 670 is compressed between the locking pin 680 and the bottom wall of the cutout 660. This position reflects that the needle 10 has now been driven into contact with the valve 650 causing upward movement of the valve 650 to the open position.

It will be appreciated that the valve 650 can be used with the locking pin 680 only and not the spring element 670 in order to provide another failsafe that prevents unintended displacement of the valve 650 from the base 610. In this arrangement, the valve 650 is inserted into the valve compartment with no spring element in the cutout 660 and then the locking pin 680 is inserted in the same manner described above with reference to the spring element embodiment. Contact between the locking pin 680 and the bottom wall of the cutout 660 prevents removal of the valve 650 from the base 610.

Figure 31:
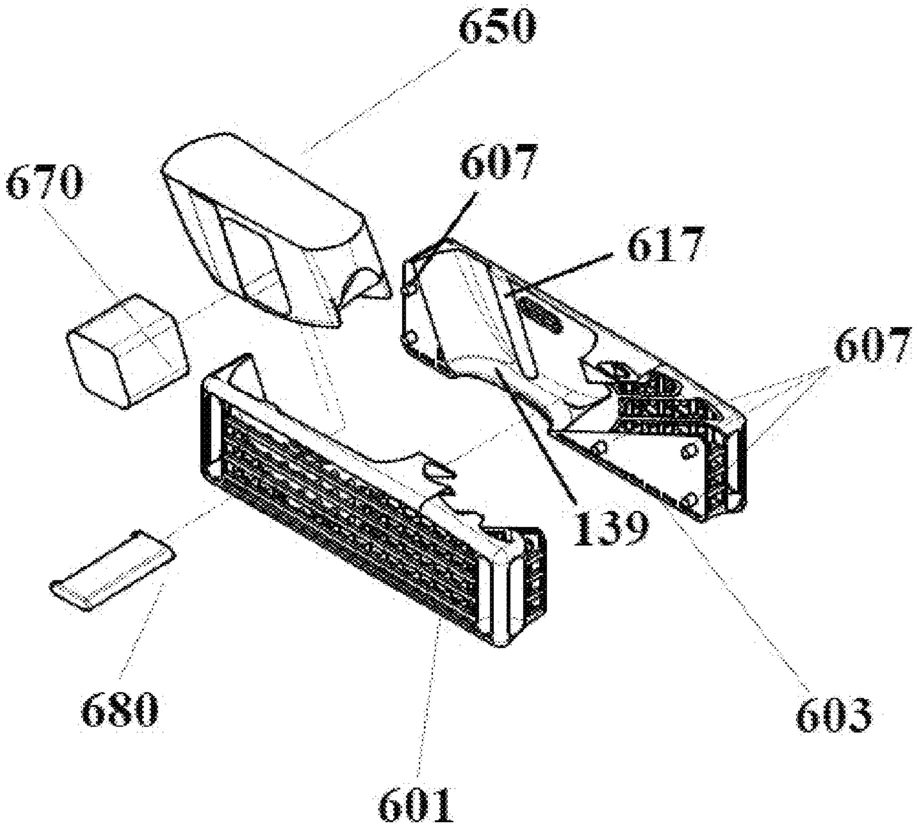
FIG. 31 is an exploded perspective view of the device of FIG. 26.
Figure 32:
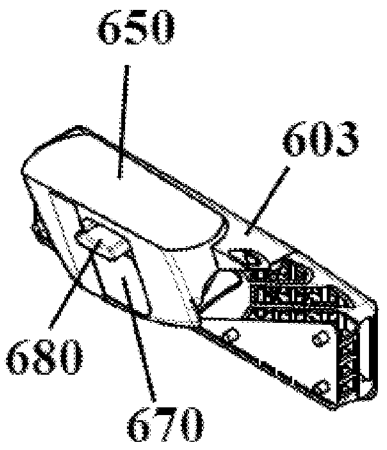
FIG. 32 is a cross-sectional perspective view of a portion of the device.

FIGS. 31 and 32 illustrate one manner in which the device can be assembled that promotes a modular arrangement and allows for the user to select the precise combination of parts. In particular, the base 610 can be formed as two separate parts that are coupled to one another. More specifically, the base 610 can be formed of a female part, identified at 601 in FIG. 31, and a male part, identified at 603 in FIG. 31. These two parts 601, 603 can mate together in a snap-fit manner. For example, the male part 603 can include press fit pins 607 that received within complementary holes (bosses) in the female part. The press fit pins 607 can be located at both ends of the male part 603.

The bottom section 139 that acts as the valve seat is bisected and formed in both parts 601, 603 so that when the two parts 601, 603 are assembled, a continuous valve seat (bottom section 139) is formed in the bottom of the valve compartment.

The modularity of the device permits different parts to be combined easily. In addition, this arrangement allows the housing unit (base 610) to be manufactured using traditional manufacturing techniques, such as injection molding, which have improved surface finish properties. Smooth surface finishing of implantable devices is important for prevention of biofilm formation and infection prevention.

Vascular Access Device 700

Figure 33:
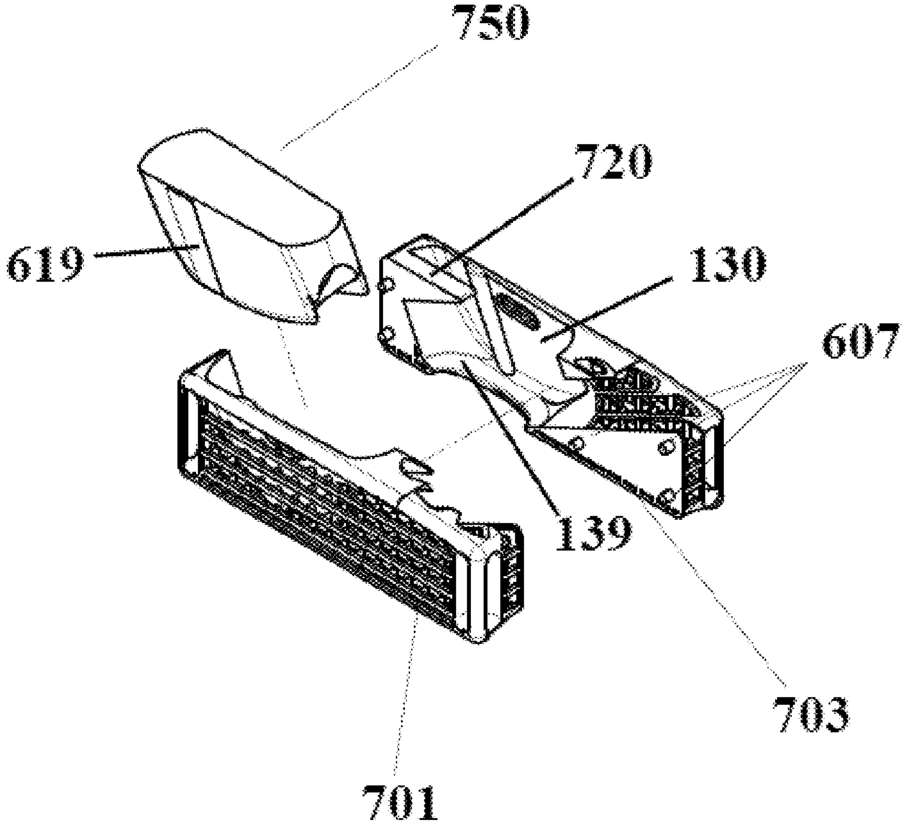
FIG. 33 is an exploded perspective view a vascular access device in accordance with a fifth embodiment.
Figure 34:
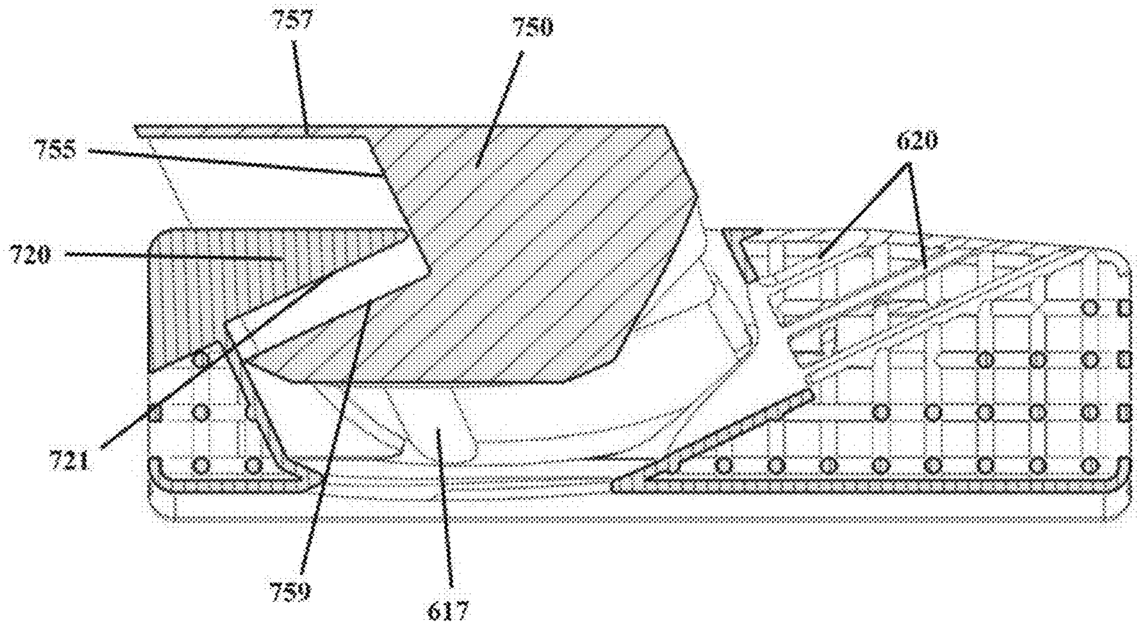
FIG. 34 is a cross-sectional view thereof.

FIGS. 33 and 34 depict a vascular access device 700 that is similar to the previously described devices and therefore, like components are numbered alike. In this embodiment, a base (housing) 710 is provided that is very similar to base 610 with the exception that the base 710 includes an integral stop 720 for restricting movement of a displaceable valve 750. As shown, the integral stop 720 represents a protrusion that extends from one end of the base into the valve compartment 130. The integral stop 720 is thus a cantilevered structure which includes a flat top that defines part of the top of the base 710 and an angled bottom surface 721. The angled bottom surface 721 faces the valve compartment 130.

The base 710 includes a first (female) part 701 which can be the same or similar to first part 601 and a second (male) part 703 which is similar to the part 603 with the exception that the second part 703 includes the integral stop 720.

The displaceable valve 750 is similar to the valve 650 but is designed to accommodate the integral stop 720. Thus, one end of the valve 750 includes a notch (cutout) 755 (FIG. 34) that receives the integral stop 720. The notch 755 is defined by a top wall 757 and a bottom wall 759 with the integral stop 720 being received therebetween. When inserted, the top wall 757 covers the integral stop 720 and the valve 750 is prevented from unintentional dislodgement by contact between the bottom surface 721 and the bottom wall 759. When these two surfaces 721, 759 contact one another, the valve 750 has reached its end of travel.

It will be appreciated that the valve 750 is intended to be used with a two part housing to allow assembly. For example, the valve 750 can be inserted into the valve compartment 130 by inserting the integral stop 720 into the notch 755 and then the first part 701 is joined and coupled to the second part 703 to capture the valve 750 therebetween.

Vascular Access Device 800

Figure 35:
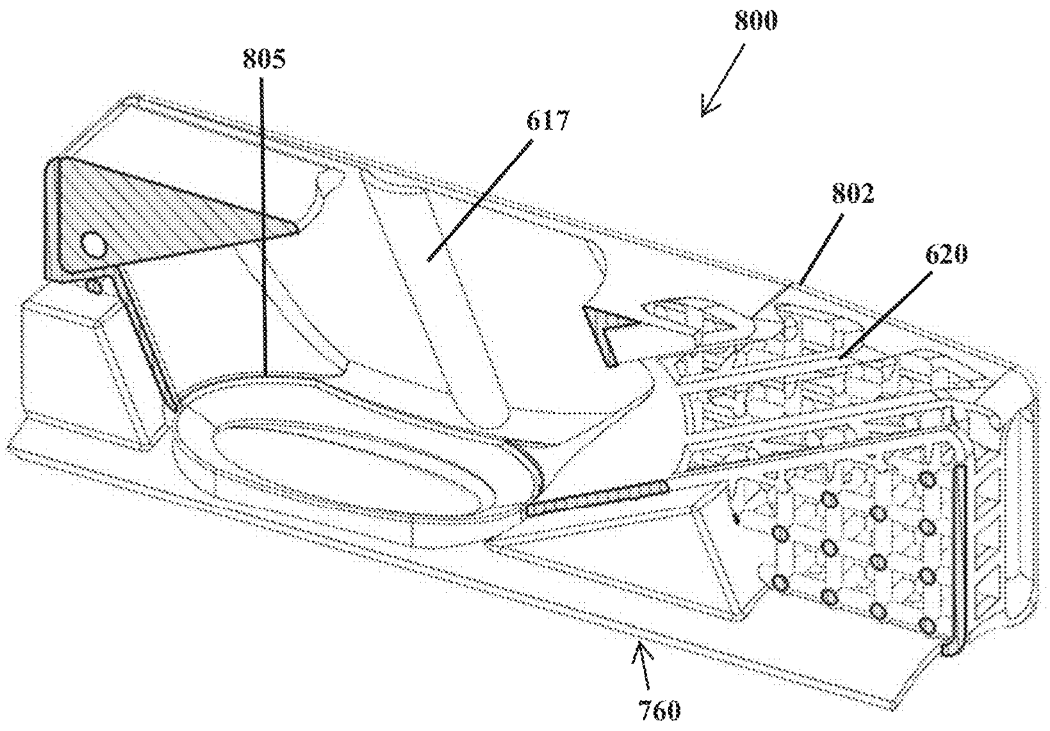
FIG. 35 is a cross-sectional partial perspective view a vascular access device in accordance with a sixth embodiment.
Figure 36:
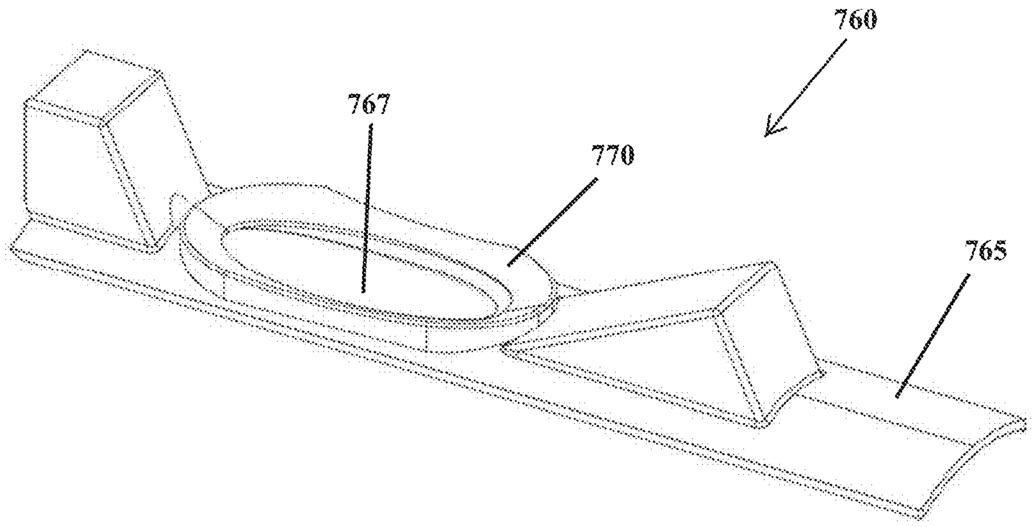
FIG. 36 is a perspective view of a bottom housing part including a valve seat and sensor arrangement for use in the device of FIG. 35.
Figure 37:
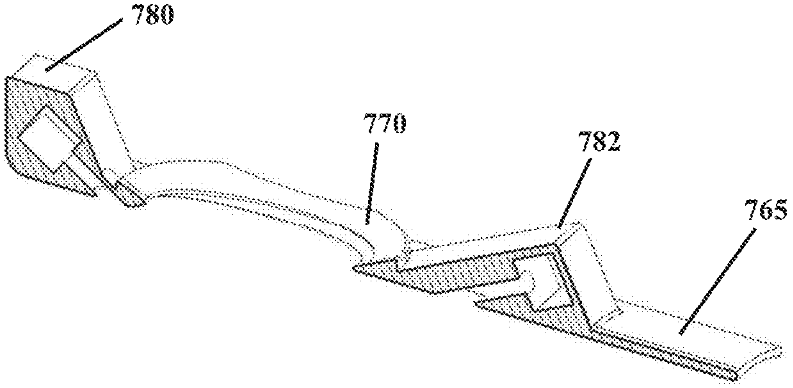
FIG. 37 is a cross-sectional view of the bottom housing part.

Now turning to FIGS. 35-37, a vascular access device 800 in accordance with another embodiment is shown. The device 800 is and can be similar in construction to other embodiments described herein. The device 800 includes four main parts, namely, the displaceable valve, such as valve 750, a first housing part (an exemplary first part is identified at 802), a second housing part and a bottom valve seat component with integral sensor which is identified at 760 in FIG. 35. In this embodiment, each of the first housing part 802 and the second housing part has a bottom opening 805 and when the two housing parts are assembled, the bottom opening 805 is a completely bounded opening the defines the needle exit.

In this embodiment, unlike forming the valve seat, such as valve seat 139, in the two housing parts, the valve seat against which the valve seals is formed in a separate part, namely, the bottom valve seat component 760 which is best shown in FIG. 36. The bottom valve seat component 760 includes a baseplate 765 that can be curved as shown so as to complement the shape of the underlying vessel. The baseplate 765 has a needle exit opening 767 through which the needle exits and contacts the target vessel. The baseplate 765 includes a valve seat 770 that surrounds the needle exit opening 767. The valve seat 770 is beveled and intended to mate with the complementary sealing bottom surface of the valve, such as the bottom seal portion 220 (outer beveled section 222).

The bottom valve seat component 760 is intended to be easily attached to the two housing parts using conventional techniques, such as a snap fit. The bottom valve seat component 760 forms the bottom section of the entire device 800 when it is assembled.

The bottom valve seat component 760 incorporates sensors into the structure and more particularly, the bottom valve seat component 760 houses all of the necessary electronics, sensors and connections in one piece, increasing surgical adaptability, reducing number of parts and preventing misconnections or incorrect installation. In the illustrated embodiment, the bottom valve seat component 760 includes a first sensor portion 780 and a second sensor portion 782. As shown in FIG. 37, the first and second sensor portions 780, 782 define housings that contain and hold the operative parts (electronics). For example, a first sensor element can be contained in (a hollow portion of) the first sensor portion 780 and a second sensor element can be contained in (a hollow portion of) the second sensor portion 782. These sensor elements can be the same as or similar to types described before (e.g., transmitter and receiver).

The two sensor elements are intended to be operatively connected via a single cable or connector. For example, a single cable can be located at one end of the device 800 to be accessed by a user (surgeon).

One other advantage of the bottom valve seat component 760 is that it aids installation of the device 800 be forming a thin baseplate 765 that can be attached to the fistula much more easily than the fully assembled device 800. For example, the bottom valve seat component 760 can be attached to the fistula using suitable adhesive or other suitable material or suitable techniques. It will be appreciated that the opening 767 can act as a window that highlights the needle entry area into the underlying fistula. This allows the surgeon to view and position the bottom valve seat component 760 at the target location. Once the bottom valve seat component 760 is secured to the fistula, the (assembled) housing unit (male/female parts) can be press fitted (i.e., clicked) onto the baseplate 765 as they are male-female counterparts.

The devices described herein provide a number of advantages including but not limited to the following:

1) End bleeding upon needle removal, eliminate infection nidus;
2) Metallic foam construction promotes tissue ingrowth, body's immune system;
3) Anti-microbial coatings eliminate biofilm infection risk; and
4) Home dialysis avoids contagion/transmission risks all together.

It is to be understood that like numerals in the drawings represent like elements through the several figures, and that not all components and/or steps described and illustrated with reference to the figures are required for all embodiments or arrangements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

What is claimed is:

1. A self-sealing vascular access device comprising:

an implantable base having a top surface and an opposite bottom surface, the implantable base having a valve compartment defined therein, the implantable base having a needle access channel formed therein and open along the top surface and the bottom surface, the valve compartment being open to the needle access channel; and a displaceable valve that is disposed within the valve compartment and movable between a lowered position in which the displaceable valve blocks the needle access channel and a raised position in which the displaceable valve is spaced from the needle access channel resulting in an opening of the needle access channel.

2. The self-sealing vascular access device of claim 1, wherein the needle access channel is formed at an acute angle relative to a longitudinal reference plane that contains opposite side edges of the bottom surface.

3. The self-sealing vascular access device of claim 1, wherein the opening of the needle access channel along the top surface has a greater area than the opening of the needle access channel along the bottom surface.

4. The self-sealing vascular access device of claim 1, wherein the implantable base includes a pair of opposite side walls and a pair of opposite end walls.

5. The self-sealing device of claim 4, wherein at least the side walls and the end walls are formed of a metallic foam material.

6. The self-sealing vascular access device of claim 1, wherein the displaceable valve moves along an axis that is at an acute angle relative to a longitudinal reference plane that contains opposite side edges of the bottom surface.

7. The self-sealing vascular access device of claim 1, wherein at least one of the displaceable valve and the implantable base includes a stop for limiting movement of the displaceable valve and preventing removal of the displaceable valve along the top surface of the implantable base.

8. The self-sealing vascular access device of claim 1, wherein the displaceable valve has slanted end walls and non-parallel side walls that extend between the end walls and prevent rotation of the displaceable valve within the implantable base.

9. The self-sealing vascular access device of claim 8, wherein one of the slanted end walls includes a contoured recess that is at least partially disposed within the needle access channel when the displaceable valve is in the lowered position.

10. The self-sealing vascular access device of claim 9, wherein the contoured recess has an arcuate shape and defines a top section of the needle access channel.

11. The self-sealing vascular access device of claim 1, wherein a bottom surface of the displaceable valve includes a flat center section and a slanted section at one end of the flat center section.

12. The self-sealing vascular access device of claim 11, wherein the slanted section lies within a plane that extends in a direction that is parallel to a longitudinal axis of the needle access channel.

13. The self-sealing vascular access device of claim 1, wherein the implantable base includes a light housing that extends transversely within and across the implantable base and a sensor housing that extends transversely within and across the implantable base.

14. The self-sealing vascular access device of claim 13, wherein one of the light housing and the sensor housing is located between a first end of the implantable base and the valve compartment and the other of the light housing and the sensor housing is located between an opposite second end of the implantable base and the valve compartment.

15. The self-sealing vascular access device of claim 14, further including an LED source disposed within the light housing and a light detector disposed within the sensor housing, wherein the LED source is configured to emit a light beam that passes through the needle access channel and is aligned with the light detector.

16. The self-sealing vascular access device of claim 1, wherein an opening of the needle access channel along the top surface is in a non-overlapping relationship relative to a second opening of needle access channel along the bottom surface.

17. The self-sealing vascular access device of claim 1, wherein the displaceable valve is displaceable within the valve compartment between the raised position and the lowered position under pressure exerted by subcutaneous tissue under which implantable base is implanted.

18. The self-sealing vascular access device of claim 1, further including a biasing element for automatically biasing the displaceable valve to the lowered position in an at rest position.

19. The self-sealing vascular access device of claim 18, wherein the biasing element comprises a spring disposed within the valve compartment.

20. The self-sealing vascular access device of claim 1, wherein the displaceable valve is hingedly coupled to the implantable base.

21. The self-sealing vascular access device of claim 20, wherein an integral hinge element of the displaceable valve provides a biasing force for automatically biasing the displaceable valve to the lowered position.

22. The self-sealing vascular access device of claim 1, wherein in the raised position, at least an upper portion of the displaceable valve is disposed above the top surface.

23. The self-sealing vascular access device of claim 1, wherein the bottom surface comprises a curved surface.

24. The self-sealing vascular access device of claim 1, wherein a top surface area of the displaceable valve is greater than a bottom surface area of the displaceable valve.

25. The self-sealing vascular access device of claim 1, wherein a distance between the lowered position and the raised position is between 1.7 mm and 2.2 mm.

26. The self-sealing vascular access device of claim 1, wherein an opening of the needle access channel along the bottom surface has an area that is less than an area of a bottom of the displaceable valve to prevent the displaceable valve from extending below the bottom surface of the implantable base.

27. The self-sealing vascular access device of claim 1, wherein the valve includes a through hole cutout that receives and holds a spring that is located between a floor of the cutout and a locking pin that passes through the cutout and is coupled to the base.

28. The seal-sealing vascular access device of claim 27, wherein the spring comprises a block formed of Polydimethylsiloxane (PDMS) material and the locking pin has lock tabs at ends thereof that engage sides of the base for securing the locking pin to the base; wherein in the lowered position, the PDMS block is not compressed, while in the raised position, the PDMS block is compressed between the locking pin and the floor of the cutout.

29. The self-sealing vascular access device of claim 1, wherein the needle access channel is defined by a plurality of needle guide rails that are arranged in a circumferential manner to define an open center configured to permit passage of a needle, the plurality of needle guides being spaced apart along a substantial length thereof to define open spaces for tissue ingrowth.

30. The self-sealing vascular access device of claim 1, wherein the base includes a pair of guide slots formed along sides thereof that receive a pair of guide ribs formed along inner walls of the base within the valve compartment.

31. The self-sealing vascular access device of claim 1, wherein the base includes an integral stop that is received within a slot formed in the valve to limit a degree to which the valve can be raised, the slot being covered by a top wall of the valve.

32. The self-sealing vascular access device of claim 1, further including a bottom valve seat component that includes a baseplate that is detachably coupled to a bottom of the base, the baseplate has a needle exit opening through which a needle can exit and a valve seat surrounds the needle exit opening, the valve seat being beveled and intended to mate with a complementary sealing bottom surface of the valve.

33. The self-sealing vascular access device of claim 32, wherein the bottom valve seat component houses sensors and connections in one piece.

34. The self-sealing vascular access device of claim 33, wherein the bottom valve seat component includes a first sensor portion that contains a first sensor element and a second sensor portion that contains a second sensor element, the valve seat and the needle exit opening being located between the first sensor element and the second sensor element.

35. The self-sealing vascular access device of claim 1, wherein the displaceable valve includes a cam surface that is disposed within the needle access channel when the displaceable valve is in the lowered position, the cam surface being configured such that an urging action of a needle inserted and advanced within the needle access channel causes displacement of the displaceable valve toward the raised position.

36. A self-sealing vascular device comprising:

an implantable perforated base having a top surface and an opposite bottom surface, the implantable base having a valve compartment defined therein and has an opening along the top surface of the implantable base, the implantable base having a needle access channel formed therein that has an opening at a first end along the top surface and has an opening at a second end along the bottom surface, the valve compartment being open to the needle access channel, wherein the opening at the first end of the needle access channel is spaced from the opening of the valve compartment along the top surface, wherein the needle access channel is defined by a plurality of needle guide rails that are arranged in a circumferential manner to define an open center configured to permit passage of a needle, the plurality of needle guides being spaced apart along a substantial length thereof to define open spaces for tissue ingrowth; and a displaceable valve that is disposed within the valve compartment and accessible along the top surface of the implantable base and being movable between a lowered position in which the displaceable valve blocks the needle access channel and a raised position in which the displaceable valve is spaced from the needle access channel resulting in the needle access channel being fully open.

37. The self-sealing vascular access device of claim 36, wherein the displaceable valve moves linearly along a first axis from the lowered position to the raised position and vice versa, the first axis being orthogonal to a longitudinal axis of the needle access channel.

38. A method of delivering a needle to a vascular site comprising the steps of:

implanting a self-sealing vascular device below subcutaneous tissue above the vascular site, the self-sealing vascular device having an implantable base having a top surface and a valve compartment defined therein and being open along the top surface of the implantable base, the implantable base having a needle access channel formed therein that is open at a first end along the top surface and is open at a second end along the bottom surface, the valve compartment being open to the needle access channel, the self-sealing device having a displaceable valve that is disposed within the valve compartment and accessible along the top surface of the implantable base, whereby pressure exerted by the overlying subcutaneous tissue causes the displaceable valve to assume a lowered position in which the displaceable valve blocks the needle access channel; and inserting the needle within the needle access channel and advancing the needle to urge the displaceable valve to a raised position which opens up the needle access channel and permits advancement of the needle to the vascular site, whereby removal of the needle from the needle access channel automatically causes the displaceable valve to move to the lowered position to block and seal the needle access channel.

39. A method of delivering a needle to a vascular site comprising the steps of:

implanting a self-sealing vascular device below subcutaneous tissue above the vascular site, the self-sealing vascular device having an implantable base having a top surface and a valve compartment defined therein and being open along the top surface of the implantable base, the self-sealing device having a displaceable valve that is disposed within the valve compartment and accessible along the top surface of the implantable base, whereby pressure exerted by the overlying subcutaneous tissue causes the displaceable valve to assume a lowered position in which the displaceable valve blocks seals a needle access channel formed in the implantable base; and inserting the needle within the needle access channel and advancing the needle to urge the displaceable valve to a raised position which opens up the needle access channel and permits advancement of the needle to the vascular site, whereby removal of the needle from the needle access channel automatically causes the displaceable valve to move to the lowered position to block and seal the needle access channel.

40. The method of claim 39, wherein the needle has a beveled distal end.

41. The method of claim 39, further including the step of biasing the displaceable valve to the lowered position prior to insertion of the needle within the needle access channel, whereby urging of the needle against the displaceable valve is sufficient to overcome a biasing force and displace the displaceable valve to the raised position.

42. A method of delivering a needle to a vascular site and automatically sealing the vascular site when the needle is removed from the vascular site, the method comprising the steps of:

positioning and securing a bottom valve seat component to a vessel wall, the bottom valve seat component including a baseplate in which a needle exit opening is formed and through which the needle can exit and a valve seat surrounds the needle exit opening, implanting a self-sealing vascular device below subcutaneous tissue above the vascular site by attaching an implantable base of the device to the baseplate, the implantable base having a needle access channel formed for receiving and permitting passage of the needle through the implantable base to the vascular site; and inserting the needle within the needle access channel and advancing the needle to urge a displaceable valve to a raised position which causes the subcutaneous tissue to locally deform and store energy, whereby removal of the needle from the needle access channel automatically causes the displaceable valve to move to a lowered position to block and seal the needle access channel as a result of downward pressure exerted by the overlying subcutaneous tissue on the displaceable valve as the stored energy is released.

* * * * *